(12) United States Patent
Sabbadini

(10) Patent No.: US 8,871,202 B2
(45) Date of Patent: *Oct. 28, 2014

(54) PREVENTION AND TREATMENT OF PAIN USING ANTIBODIES TO SPHINGOSINE-1-PHOSPHATE

(75) Inventor: Roger A. Sabbadini, Lakeside, CA (US)

(73) Assignee: Lpath, Inc., San Diego, CA (US)

( * ) Notice: Subject to any disclaimer, the term of this patent is extended or adjusted under 35 U.S.C. 154(b) by 68 days.

This patent is subject to a terminal disclaimer.

(21) Appl. No.: 13/246,704

(22) Filed: Sep. 27, 2011

(65) Prior Publication Data
US 2012/0082665 A1 Apr. 5, 2012

Related U.S. Application Data

(63) Continuation-in-part of application No. 12/258,383, filed on Oct. 24, 2008, now Pat. No. 8,026,342.

(51) Int. Cl.
*A61K 39/395* (2006.01)
*C07K 16/44* (2006.01)
*A61K 39/00* (2006.01)

(52) U.S. Cl.
CPC ............ *C07K 16/44* (2013.01); *C07K 2317/56* (2013.01); *C07K 2317/565* (2013.01); *C07K 2317/24* (2013.01); *A61K 2039/505* (2013.01)
USPC .................. 424/130.1; 424/133.1; 424/141.1

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. |
| 4,150,949 A | 4/1979 | Smith |
| 4,179,337 A | 12/1979 | Davis et al. |
| 4,275,149 A | 6/1981 | Litman et al. |
| 4,301,144 A | 11/1981 | Iwashita et al. |
| 4,318,980 A | 3/1982 | Boguslaski et al. |
| RE30,985 E | 6/1982 | Cartaya |
| 4,376,110 A | 3/1983 | David et al. |
| 4,485,045 A | 11/1984 | Regen |
| 4,496,689 A | 1/1985 | Mitra |
| 4,544,545 A | 10/1985 | Ryan et al. |
| 4,560,655 A | 12/1985 | Baker |
| 4,640,835 A | 2/1987 | Shimizu et al. |
| 4,657,866 A | 4/1987 | Kumar |
| 4,670,417 A | 6/1987 | Iwasaki et al. |
| 4,676,980 A | 6/1987 | Segal et al. |
| 4,737,456 A | 4/1988 | Weng et al. |
| 4,767,704 A | 8/1988 | Cleveland et al. |
| 4,791,192 A | 12/1988 | Nakagawa et al. |
| 4,816,397 A | 3/1989 | Boss et al. |
| 4,816,450 A | 3/1989 | Bell et al. |
| 4,816,567 A | 3/1989 | Cabilly et al. |
| 4,927,762 A | 5/1990 | Darfler |
| 4,937,232 A | 6/1990 | Bell et al. |
| 5,013,556 A | 5/1991 | Woodle et al. |
| 5,079,263 A | 1/1992 | Zeeck et al. |
| 5,122,469 A | 6/1992 | Mather et al. |
| 5,137,919 A | 8/1992 | Igarashi et al. |
| 5,151,360 A | 9/1992 | Handa et al. |
| 5,204,244 A | 4/1993 | Fell et al. |
| 5,225,539 A | 7/1993 | Winter |
| 5,229,275 A | 7/1993 | Goroff |
| 5,248,824 A | 9/1993 | Igarashi et al. |
| 5,260,288 A | 11/1993 | Igarashi et al. |
| 5,331,014 A | 7/1994 | Kimura et al. |
| 5,369,030 A | 11/1994 | Hannun et al. |
| 5,391,800 A | 2/1995 | Igarashi et al. |
| 5,430,160 A | 7/1995 | Holton |
| 5,444,087 A | 8/1995 | Patel et al. |
| 5,530,101 A | 6/1996 | Queen et al. |
| 5,534,615 A | 7/1996 | Baker et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,573,905 A | 11/1996 | Lerner et al. |
| 5,585,089 A | 12/1996 | Queen et al. |
| 5,585,476 A | 12/1996 | MacLennan |
| 5,589,369 A | 12/1996 | Seidman et al. |
| 5,591,669 A | 1/1997 | Krimpenfort et al. |
| 5,624,821 A | 4/1997 | Winter et al. |
| 5,627,171 A | 5/1997 | Park et al. |
| 5,663,404 A | 9/1997 | Igarashi et al. |
| 5,667,337 A | 9/1997 | Lazes |
| 5,677,288 A | 10/1997 | Marangos |
| 5,693,761 A | 12/1997 | Queen et al. |
| 5,693,762 A | 12/1997 | Queen et al. |
| 5,714,350 A | 2/1998 | Co et al. |
| 5,731,168 A | 3/1998 | Carter et al. |
| 5,777,085 A | 7/1998 | Co et al. |
| 5,834,597 A | 11/1998 | Tso et al. |

(Continued)

FOREIGN PATENT DOCUMENTS

CA 2019559 C 12/1990
EP 0173648 A2 3/1986

(Continued)

OTHER PUBLICATIONS

Kohler, Practical Oncology, 2003, 148-156, 4(3).
Dickson et al., Methods Enzymol., 1999, 3-9, 311.
Dobrowsky, Cell Signal., 2000, 81-90, 12(2).
Doherty et al., Bioconjug. Chem., 2005, 1291-1298, 16(5).
Dougherty et al., Cornea, 1996, 537-540, 15(5).
Doyle et al., FASEB J., 2011, 2782-2791, 25(8).
Doyle et al., Neurosci. Lett., 2011, 4-8, 499(1).
Doyle et al., Pain, 2011, 643-648, 152(3).
Dressler et al., Science, 1992, 1715-1718, 255(5052).
Dubner et al., Trends Neurosci., 1992, 96-103, 15(3).
Edsall et al., Biochem., 1998, 12892-1289, 37(37).

(Continued)

*Primary Examiner* — Yunsoo Kim
(74) *Attorney, Agent, or Firm* — Acuity Law Group, P.C.; Daniel M. Chambers

(57) ABSTRACT

The present invention relates to use of anti-S1P agents, for example, humanized monoclonal antibodies, for prevention and/or treatment of pain, including neuropathic pain, hyperalgesia, allodynia, and chemotherapy-induced pain.

4 Claims, 2 Drawing Sheets

(56) References Cited

U.S. PATENT DOCUMENTS

| | | |
|---|---|---|
| 5,851,782 A | 12/1998 | Hannun et al. |
| 5,861,155 A | 1/1999 | Lin |
| 5,882,644 A | 3/1999 | Chang et al. |
| 5,919,687 A | 7/1999 | Chatterjee |
| 5,929,039 A | 7/1999 | Woodcock et al. |
| 5,932,448 A | 8/1999 | Tso et al. |
| 5,989,803 A | 11/1999 | Tabas et al. |
| 6,013,256 A | 1/2000 | Light et al. |
| 6,051,598 A | 4/2000 | Shayman et al. |
| 6,057,126 A | 5/2000 | Munroe et al. |
| 6,096,871 A | 8/2000 | Presta et al. |
| 6,129,914 A | 10/2000 | Weiner et al. |
| 6,130,067 A | 10/2000 | Tsui |
| 6,140,060 A | 10/2000 | Chun et al. |
| 6,180,370 B1 | 1/2001 | Queen et al. |
| 6,187,562 B1 | 2/2001 | Duckworth et al. |
| 6,210,671 B1 | 4/2001 | Co |
| 6,210,976 B1 | 4/2001 | Sabbadini |
| 6,284,798 B1 | 9/2001 | Amtmann et al. |
| 6,306,911 B1 | 10/2001 | Wachter et al. |
| 6,323,201 B1 | 11/2001 | Carson et al. |
| 6,329,511 B1 | 12/2001 | Vasquez et al. |
| 6,342,221 B1 | 1/2002 | Thorpe et al. |
| 6,350,861 B1 | 2/2002 | Co et al. |
| 6,352,844 B1 | 3/2002 | Maurer et al. |
| 6,407,213 B1 | 6/2002 | Carter et al. |
| 6,423,527 B1 | 7/2002 | Saba et al. |
| 6,479,284 B1 | 11/2002 | Marasco et al. |
| 6,500,931 B1 | 12/2002 | Tempest et al. |
| 6,534,322 B1 | 3/2003 | Sabbadini |
| 6,534,323 B1 | 3/2003 | Sabbadini |
| 6,548,640 B1 | 4/2003 | Winter |
| 6,571,638 B2 | 6/2003 | Hines et al. |
| 6,610,835 B1 | 8/2003 | Liotta et al. |
| 6,613,322 B2 | 9/2003 | Tabas et al. |
| 6,639,055 B1 | 10/2003 | Carter et al. |
| 6,649,362 B2 | 11/2003 | Gamble et al. |
| 6,858,383 B2 | 2/2005 | Sabbadini |
| 6,881,546 B2 | 4/2005 | Sabbadini |
| 7,060,808 B1 | 6/2006 | Goldstein et al. |
| 7,087,409 B2 | 8/2006 | Barbas, III et al. |
| 7,169,390 B2 | 1/2007 | Sabbadini |
| 2001/0041688 A1 | 11/2001 | Waeber et al. |
| 2002/0150582 A1 | 10/2002 | Friedrichs et al. |
| 2003/0096022 A1 | 5/2003 | Sabbadini |
| 2003/0125533 A1 | 7/2003 | Kossida et al. |
| 2003/0219782 A1 | 11/2003 | Saba et al. |
| 2003/0229208 A1 | 12/2003 | Queen et al. |
| 2005/0226862 A1 | 10/2005 | Sabbadini |
| 2007/0148168 A1 | 6/2007 | Sabbadini et al. |
| 2008/0213274 A1 | 9/2008 | Sabbadini et al. |
| 2009/0176263 A1 | 7/2009 | Mandala et al. |

FOREIGN PATENT DOCUMENTS

| | | |
|---|---|---|
| EP | 0244234 A2 | 11/1987 |
| EP | 0402226 A1 | 12/1990 |
| EP | 0125023 B1 | 6/1991 |
| EP | 0183070 A2 | 10/1991 |
| EP | 0173663 B1 | 1/1992 |
| EP | 0519596 A1 | 12/1992 |
| EP | 0120694 B1 | 7/1993 |
| EP | 0194276 B1 | 8/1993 |
| EP | 0239400 B1 | 8/1994 |
| JP | 1987 09-110722 A | 4/1987 |
| JP | 2000-293181 A | 10/2000 |
| WO | 86/01533 A1 | 3/1986 |
| WO | 87/00195 A1 | 1/1987 |
| WO | 90/03430 A1 | 4/1990 |
| WO | 93/11161 A1 | 6/1993 |
| WO | 96/27011 A1 | 9/1996 |
| WO | 96/32478 A1 | 10/1996 |
| WO | 97/44019 A1 | 11/1997 |
| WO | 98/03529 A1 | 1/1998 |
| WO | 98/28445 A1 | 7/1998 |
| WO | 98/40349 A1 | 9/1998 |
| WO | 98/57179 A1 | 12/1998 |
| WO | 99/07855 A1 | 2/1999 |
| WO | 99/12890 A1 | 3/1999 |
| WO | 99/16888 A2 | 4/1999 |
| WO | 99/33972 A1 | 7/1999 |
| WO | 99/38983 A1 | 8/1999 |
| WO | 99/41265 A1 | 8/1999 |
| WO | 99/41266 A1 | 8/1999 |
| WO | 99/46277 A1 | 9/1999 |
| WO | 99/61581 A2 | 12/1999 |
| WO | 00/00593 A2 | 1/2000 |
| WO | 00/21919 A1 | 4/2000 |
| WO | 00/40262 A1 | 7/2000 |
| WO | 00/52173 A2 | 9/2000 |
| WO | 00/56135 A2 | 9/2000 |
| WO | 00/58448 A1 | 10/2000 |
| WO | 00/58491 A1 | 10/2000 |
| WO | 00/59517 A1 | 10/2000 |
| WO | 00/70028 A1 | 11/2000 |
| WO | 00/72833 A2 | 12/2000 |
| WO | 01/04108 A1 | 1/2001 |
| WO | 01/04139 A2 | 1/2001 |
| WO | 01/07418 A2 | 2/2001 |
| WO | 01/31029 A2 | 5/2001 |
| WO | 01/38295 A1 | 5/2001 |
| WO | 01/55410 A2 | 8/2001 |
| WO | 01/57057 A1 | 8/2001 |
| WO | 01/60990 A2 | 8/2001 |
| WO | 01/71045 A2 | 9/2001 |
| WO | 01/72701 A1 | 10/2001 |
| WO | 01/80903 A1 | 11/2001 |
| WO | 01/85953 A1 | 11/2001 |
| WO | 2006/105062 A2 | 10/2006 |
| WO | 2007/053447 A2 | 5/2007 |

OTHER PUBLICATIONS

Edson et al., Mayo Clin. Proc., 1999, 519-528, 74(5).
Eichler et al., Med. Res. Rev., 1995, 481-496, 15(6) (Abstract Only).
Eichler et al., Curr. Pharm. Des., 2006, 2645-2660, 12(21).
El-Asrar et al., Am. J. Ophthalmol., 2004, 401-411, 138(3).
Eljarrat-Binstock et al., J. Control. Release, 2006, 479-489, 110(3).
Eppstein et al., Proc. Natl. Acad. Sci. USA, 1985, 3688-3692, 82(11).
Erber et al., FASEB J., 2004, 338-340, 18(2).
Espinosa-Heidmann et al., Invest. Ophthalmol. Vis. Sci., 2003, 3586-3592, 44(8).
Felinski et al., Curr. Eye Res., 2005, 949-957, 30(11).
Fensome et al., J. Biol. Chem., 2000, 1128-1136, 275(2).
Fini, Prog. Retin. Eye Res., 1999, 529-551, 18(4).
Flatters et al., Pain, 2006, 245-257, 122(3).
Folger et al., Invest. Ophthalmol. Vis. Sci., 2001, 2534-2541, 42(11).
Fontana et al., Ophthalmology, 2006, 930-936, 113(6).
Foote et al., J. Mol. Biol., 1992, 487-499, 224(2).
Forni et al., Cancer Res., 2000, 2571-2575, 60(10).
Forrester, Nat. Med., 2003, 1350-1351, 9(11).
French et al., Cancer Res., 2003, 5962-5969, 63(18).
Freyberger et al., Exp. Clin. Endocrinol. Diabetes, 2000, 106-109, vol. 108(2).
Fujii et al., J. Biochem (Tokyo), 1998, 1178-1187, 124(6).
Fukushima et al., Proc. Natl. Acad. Sci. USA, 1998, 6151-6156, 95(11).
Furneisen et al., Biochim. Biophys. Acta, 2000, 71-82, 1484(1).
Gaga et al., J. Immunol., 1991, 816-822, 147(3).
Garcia-Ruiz, Hepatology, 2000, 56-65, 32(1).
Gardell et al., Trends Mol. Med., 2006, 65-75, 12(2).
Gariano et al., Nature, 2005, 960-966, 438(7070).
Gates et al., Toxicon., 1990, 1303-1315, 28(11).
Gatt et al., J. Neurochem., 1978, 547-550, 31(2).
Gavrilenko et al., Bioorg. Khim., 1993, 133-138, 19(1) (English Abstract Only).
Geeraert et al., Biochem. J., 1997, 125-132, 327(1).
George et al., Pain, 2000, 267-275, 88(3).
Gerhardt et al., Cell Tissue Res., 2003, 15-23, 314(1).
Ghate et al., Exp. Opin. Drug Deliv., 2006, 275-287, 3(2).
Ghosh et al., J. Biol. Chem., 1987, 12550-12556, 262(26).

(56) References Cited

OTHER PUBLICATIONS

Ghosh et al., Mol. Cell. Biochem., 1998, 161-168, 189(1-2).
Gilmore et al., J. Bacterial., 1989, 744-753, 171(2).
Glickman et al., Mol. Cel. Neurosci., 1999, 141-152, 14(2).
Goetzl et al., Faseb J., 1998, 1589-1598, 12(15).
Goetzl et al., Adv. Exp. Med. Biol., 1999, 259-264, 469.
Gonda, et al., Biochem. J., 1999, 67-75, 337(1).
Maceyka et al., Biochim. Biophys. Acta, 2002, 193-201, 1585(2-3).
Magnelli et al., Biochem. Biophys. Res. Comm., 1994, 84-90, 204(1).
Mair et al., PLoS One, 2011, e17268, 6(2).
Mandala et al., J. Antibiot. (Tokyo), 1994, 376-379, 47(3).
Mandala et al., J. Antibiot. (Tokyo), 1995, 349-356, 48(5).
Mandala et al., J. Antibiot. (Tokyo), 1997, 339-343, 50(4).
Mandala et al., J. Biol. Chem., 1997, 32709-32714, 272(51).
Mandala et al., Proc. Natl. Acad. Sci. USA, 1998, 150-155, 95(1).
Mandala et al., Methods Enzymol., 1999, 335-348, 311.
Mandala et al., Proc. Natl. Acad. Sci. USA, 2000, 7859-7864, 97(14).
Mandala et al., Prostaglandins Other Lipid Mediat., 2001, 143-156, 64(1-4).
Mao et al., Proc. Natl. Acad. Sci. USA, 1996, 1993-1996, 93(5).
Mao et al., J. Biol. Chem., 2000, 31369-31378, 275(40).
Mao et al., J. Biol. Chem., 2000, 6876-6884, 275(10).
Mao et al., J. Biol. Chem., 2001, 26577-26588, 276(28).
Marcovich et al., Curr. Eye Res., 2002, 17-22, 25(1).
Marks et al., J. Mol. Biol., 1991, 581-597, 222(3).
Marks et al., Methods Enzymol., 1999, 50-59, 311.
Martin et al., J. Bioenerg. Biomembr., 2001, 143-153, 33(2).
Mather, Biol. Reprod., 1980, 243-252, 23(1).
Mather et al., Ann. NY Acad. Sci., 1982, 44-68, 383.
Matsumoto et al., Rheumatol. Int., 2006, 1096-1100, 26(12).
Meacci et al., FEBS Lett., 1999, 184-188, 457(2).
Meldrum, Am. J. Physiol., 1998, R577-R595, 274(3).
Melendez et al., Gene, 2000, 19-26, 251(1).
Mendel et al., Eur. J. Immunol., 1995, 1951-1959, 25(7).
Meroni et al., J. Androl., 1999, 619-625, 20(5).
Merrill Jr. et al., Adv. Lipid Res., 1993, 215-234, 26.
Merrill Jr. et al., J. Lipid Res., 1993, 617-622, 26(5).
Michel et al., J. Biol. Chem., 1997, 22432-22437, 272(36).
Millan, Prog. Neurobiol., 1999, 1-164, 57(1).
Milstien et al., Cancer Cell., 2006, 148-150, 9(3).
Mingeot-Leclercq et al., Antimicrob. Agents Chemother., 1999, 727-734, 43(4).
Mingeot-Leclercq et al., Antimicrob. Agents Chemother., 1999, 1003-1012, 43(5).
Mitsutake et al., J. Biol. Chem., 2001, 26249-26259, 276(28).
Miyake, Biochem. Biophys. Res. Commun., 1995, 396-403, 211(2).
Mohan et al., Biochem. Biophys. Acta, 1984, 339-342, 777(2).
Mohler et al., J. Immunol., 1993, 1548-1561, 151(3).
Morea et al., Methods, 2000, 267-279, 20(3).
Morimoto et al., J. Biochem. Biophys. Methods, 1992, 107-117, 24(1-2).
Morrison et al., Proc. Natl. Acad. Sci. USA, 1984, 6851-6855, 81(21).
Munson et al., Anal. Biochem., 1980, 220-239, 107(1).
Murata et al., Anal. Biochem., 2000, 115-120, 282(1).
Murphy et al.(Ed.), Janeway's Immunobiology, Fifth Edition, 2001, Garland Publishing, London, UK (Electronic Table of Contents Only).
Mutsch et al., Graefes Arch. Clin. Exp. Ophthalmol., 2000, 884-891, 238(11).
Myers et al., Drug Disc. Today, 2006, 8-20, 11(1-2).
Myles et al., Adv. Drug Deliv. Rev., 2005, 2063-2079 57(14).
Nagineni et al., J. Cell Physiol., 2005, 35-43, 203(1).
Nakajima et al., Biophysical J., 2000, 319A, 78(1, Part 2).
Nakajima et al., Eur. J. Biochem., 2000, 5679-5686, 267(18).
Abe et al., J. Lipid Res., 1995, 611-621, 36(3).
Abe et al., Anal. Biochem., 2000, 344-347, 287(2).
Abe et al., Kidney Int., 2000, 446-454, 57(2).
Adam et al., J. Bio. Chem., 1996, 14617-14622, 271(24).
Akiyama et al., J. Cell Physiol., 2006, 407-412, 207(2).
Allende et al., Biochim Biophys Acta, 2002, 222-227, 1582(1-3).
Ambati, Surv. Ophthalmol., 2003, 257-293, 48(3).
Amin et al., Invest. Ophthalmol. Vis. Sci., 1994, 3178-3188, 35(8).
An, Ann. NY Acad. Sci., 2000, 25-33, 905(1).
An et al., FEBS Letts., 1997, 279-282, 417(3).
An et al., J. Biol. Chem., 1998, 7906-7910, 273(14).
An et al., J. Cell. Biochem. Suppl., 1998, 147-157, 72(S30-S31).
An et al., J. Biol. Chem., 2000, 288-296, 275(1).
Ancellin et al., J. Biol. Chem., 2001, 6667-6675, 277(8).
Andrews et al., Ophthalmol. Vis. Sci. 1999, 2683-2689, 40(11).
Andrieu-Abadie et al., FASEB J., 1999, 1501-1510, 13(12).
Annabi et al., Exp. Hematol., 2003, 640-649, 31(7).
Arenz et al., Angew. Chem. Int. Ed., 2000, 1440-1442, 39(8).
Arenz et al., Bioorg. Medicinal Chem., 2001, 2901-2904, 9(11).
Arenz et al., Chem. Biochem., 2001, 141-143, 2(2).
Arenz et al., Eur. J. Org. Chem., 2001, 137-140, 2001(1).
Argraves et al., J. Bio. Chem., 2004, 50580-50590, 279(48).
Ariga et al., J. Lip. Res., 1998, 1-16, 39(1).
Armulik et al., Circ. Res., 2005, 512-513, 97(6).
Arruda et al., Brain Res., 2000, 216-225, 879(1-2).
Asahara et al., Circ. Res., 1998, 233-240, 83(3).
Bajjalieh et al., Methods Enzymol., 1999, 207-215, 311.
Baranauskas et al., Prog. Neurobiol., 1998, 349-365, 54(3).
Barbone et al., Meth. Enzymol., 1999, 168-176, 311.
Barnes et al., Anal. Biochem., 1980, 255-270, 102(2).
Baroni et al., New Engl. J. Med., 2006, 2667-2676, 354(25).
Baudhuin et al., FASEB J., 2004, 341-343, 18(2).
Bawab et al., J. Biol. Chem., 2000, 21508-21513, 275(280).
Becerril et al., Ophthalmology, 2005, pg. 2238, 112(12).
Benjamin et al., Development, 1998, 1591-1598, 125(9).
Berge et al., J. Pharm. Sci., 1977, 1-19, 66, (1).
Bergers et al., Neuro-oncol., 2005, 452-464, 7(4).
Bernardo et al., J. Biol. Chem., 2000, 7641-7647, 275(11).
Betto et al., Biochem. J., 1997, 327-333, 322(1).
Bielawska et al., Am. J. Pathol., 1997, 1257-1263, 151(5).
Bielawska et al., J. Biol. Chem., 1996, 12646-12654, 271(21).
Bodey et al., Anticancer Res., 2000, 2665-2676, 20(4).
Bohler et al., Nephrol. Dial. Transplant., 2004, 702-713, 19(3).
Bohler et al., Transplantation, 2005, 492-495, 79(4).
Boudker et al., J. Biol. Chem., 1993, 22150-22155, 268(29).
Boulton et al., Br. J. Ophthalmol., 1997, 228-233, 81(3).
Boushey et al., Environ. Health Perspect., 1995, 229-233, 103(6).
Brady et al., Proc. Natl. Acad. Sci. USA, 1966, 366-369, 55(2).
Brennan et al., Science, 1985, 81-83, 229(4708).
Brindley et al., Methods Enzymol., 1999, 233-244, 311.
Napoli et al., J. Clin. Bas. Cardiol., 1998, 37-42, 1(1).
Nava et al., Exp. Cell Res., 2002, 115-127, 281(1).
Netto et al., Cornea, 2005, 509-522, 24(5).
Neuberger et al., Nature, 1984, 604-608, 312(5995).
Nikolova-Karakashian et al., Meth. Enzymol., 1999, 194-201, 311.
Norata et al., Circulation, 2005, 2805-2811, 111(21).
Obeid et al., Science, 1993, 1769-1771, 259(5102).
Oh et al., Invest. Ophthalmol. Vis. Sci., 1999, pp. 1891-1898, 40(9).
Ohta et al., FEBS Lett., 1994, 267-270, 355(3).
Ohta et al., Cancer Res., 1995, 691-697, 55(3).
Okamoto et al., J. Biol. Chem., 1998, 27104-27110, 273(42).
Okamoto et al., Biochem. Biophys. Res. Commun., 1999, 203-208, 260(1).
Okazaki et al., J. Biol. Chem., 1994, 4070-4077, 269(6).
Okino et al., J. Biol. Chem., 1999, 36616-36622, 274(51).
Olivera et al., Nature, 1993, 557-560, 365(6446).
Olivera et al., Methods Enzymol., 1999, 215-223, 311.
Olshefski et al., Int. J. Cancer, 2001, 131-138, 93(1).
Oral et al., J. Biol. Chem., 1997, 4836-4842, 272(8).
Osol et al., Ed., Remington's Pharmaceutical Sciences 19th Ed., 1995, Mack Publishing, Easton, PA, USA (Table of Contents Only).
O'Sullivan et al., Methods Enzymol., 1981, 147-166, 73(B).
Otani et al., Invest. Ophthalmol. Vis. Sci., 1999, 1912-1920, 40(9).
Paik et al., Genes Dev., 2004, 2392-2403, 18(19).
Parrill et al., J. Biol. Chem., 2000, 39379-39384, 275(50).
Pauleikhoff, Retina, 2005, 1065-1084, 25(8).
Pchejetski et al., Cancer Res., 2005, 11667-11675, 65(24).

(56) References Cited

OTHER PUBLICATIONS

Pchejetski et al., Mol. Cancer Ther., 2008, 1836-1845, 7(7).
Pitson et al., Biochem J., 2000, 429-441, 350(2).
Pitson et al., J. Biol. Chem., 2000, 33945-33950, 275(43).
Planck et al., Curr. Eye Res., 1992, 1031-1039, 11(11).
Polomano et al., Pain, 2001, 293-304, 94(3).
Pournaras et al., Klin. Monatsbl. Augenheilkd., 1998, 356-358, 212(5 (English Abstract Only).
Presta, Curr. Opin. Struct. Biol., 1992, 593-596, 2(6).
Presta et al., Canc. Res., 1997, 4593-4599, 57(20).
Pyne et al., Biochem. J., 2000, 385-402, 349(2).
Queen et al., Proc. Natl. Acad. Sci. USA, 1989, 10029-10033, 86(24).
Raag et al., FASEB J., 1995, 73-80, 9(1).
Rani et al., J. Biol. Chem., 1995, 2859-2867, 270(6).
Rath et al., J. Clin. Immunol., 1999, 350-364, 19(6).
Razzaque et al., Invest. Ophthalmol. Vis. Sci., 2004, 1174-1181, 45(4).
Riechmann et al., Nature, 1988, 323-327, 332(6162).
Riley et al., Toxicol. Appl. Pharmacol., 1993, 105-112, 118(1) (Abstract Only).
Riley et al., Meth. Enzymol., 1999, 348-361, 311.
Robaye et al., Am. J. Pathol., 1991, 447-453, 138(2).
Robbins et al., Invest. Ophthalmol. Vis. Sci., 1994, 3649-3663, 35(10).
Romiti et al., Mol. Cell. Biochem., 2000, 75-81, 205(1-2).
Rosenfeld et al., N. Eng. J. Med., 2006, 1419-1431, 355(14).
Rudikoff et al., Proc. Natl. Acad. Sci. USA, 1982, 1979-1983, 79(6).
Runcie at al, Organic Lett., 2001, 3237-3239, 3(21).
Sabbadini et al., Biochem. Biophys. Res. Comm., 1993, 752-758, 193(2).
Sabbadini et al., Circulation, 2000, 11699, 102(18 Suppl.).
Kostelny et al., J. Immunol., 1992, 1547-1553, 148(5).
Kotani et al., New Engl. J. Med., 2000, 1514-1519, 343(21).
Kozbor et al., J. Immunol., 1984, 3001-3005, 133(6).
Krag et al., Acta Ophthalmol. (Copenh.), 1992, 530-533, 70(4).
Kria et al., Graefes Arch. Clin. Exp. Ophthalmol., 1998, 702-708, 236(9).
Kronke, Chem. Phys. Lipids, 1999, 157-166, 102(1-2).
Krown et al., J. Clin. Invest., 1996, 2854-2865, 98(12).
Kubota et al., Japan J. Exp. Med., 1989, 59-64, 59(2).
Kubota et al., Neurol. Res., 1996, 337-341, 18(4).
Kwon et al., J. Biol. Chem., 2001, 10627-10633, 276(14).
La Cour et al., Drugs Aging, 2002, 101-133, 19(2).
La Heij et al., Am. J. Ophthal., 2002, 367-375, 134(3).
Lanterman et al., Biochem. J., 1998, 525-531, 332(2).
Lazar et al., Mol. Cell. Biol., 1988, 1247-1252, 8(3).
Lee et al., Biochem. J., 1998, 457-461, 334(2).
Lee et al., Circ., 1988, 1047-1051, 78(4).
Lee et al., Science, 1998, 1552-1555, 279(5356).
Lee et al., Biochem. Biophys. Res. Commun., 1999, 743-750, 264(3).
Lee et al., Cell, 1999, 301-312, 99(3).
Lee et al., J. Bio. Chem., 1999, 14662-14669, 274(21).
Lee et al., Am. J. Physiol. Cell Physiol., 2000, C612-C618, 278(3).
Lee et al., Cornea, 2001, 738-742, 20(7).
Leung et al., J. Neuroinflamm., 2010, 27, 7(1).
Levade, et al., J. Clin. Chem. Clin. Biochem., 1986, 205-220, 24(4).
Levade et al., Circ. Res., 2001, 957-968, 89(11).
Lewin, Genes IV, 1990, 810, Oxford University Press.
Li et al., Genomics, 1999, 223-231, 62(2).
Liliom at al, Biochem. J., 2001, 189-197, 355(1).
Lin et al., Febs Lett., 1998, 249-253, 423(2).
Lindahl et al., Science, 1997, 242-245, 277(5323).
Lindmark et al., J. Immunol. Meth., 1983, 1-13, 62(1).
Lingen, Arch. Pathol. Lab Med., 2001, 67-71, 125(1).
Linn et al., Biochem. Soc., 2001, 831-835, 29(6).
Lister et al., Biochim. Biophys. Acta, 1995, 25-30, 1256(1).
Little at al, Biotechn. Adv., 1994, 539-555, 12(3).
Liu et al., J. Biol. Chem., 1997, 16281-16287, 272(26).
Liu et al., Semin. Cell Dev. Biol., 1997, 311-322, 8(3).
Liu et al., J. Biol. Chem., 1998, 11313-11320, 273(18).
Liu et al., J. Biol. Chem., 1998, 34472-34479, 273(51).
Liu et al., Crit. Rev. Clin. Lab. Sci., 1999, 511-573, 36(6).
Liu et al., J. Biol. Chem., 2000, 19513-19520, 275(26).
Liu et al., Meth. Enzymol., 2000, 164-167, 311.
Liu et al., Curr. Opin. Ophthalmol., 2004, 221-226, 15(3).
Lochhead at al, Kidney Int., 1998, 373-381, 54(2).
Long et al., Prostaglandins Other Lipid Mediat., 2006, 74-80, 80(1-2).
Luberto et al., J. Biol. Chem., 1998, 14550-14559, 273(23).
Luberto et al., Lipids, 1999, S5-S11, 34(Suppl. 1).
Luberto et al., J. Biol. Chem., 2002, 41128-41139, 277(43).
Lynch at al., Trends Pharmacol. Sci., 1999, 473-475, 20(12).
MacCallum et al., J. Mol. Biol., 1996, 732-745, 262(5).
Brown et al., N. Eng. J. Med., 2006, 1432-1444, 355(14).
Brownlee, Current Biol., R535-R538, 2001, 11(13).
Burgess et al., J. Cell Biol., 1990, 2129-2138, 111(5).
Burkhart et al, J. Natl. Cancer Inst., 2003, 1394-1403, 95(18).
Burton et al., Adv. Immunol., 1994, 191-280, 57.
Butrus et al., Am. J. Ophthalmol., 1995, 236-237, 119(2).
Butt et al., Eur. J. Cell Biol., 1995, 330-335, 68(3).
Byers, CA Canc. J., 1999, 353-361, 49(6).
Bylsma et al., Clin. Exp. Optom., 2005, 322-334 88(5).
Cain et al., J. Mol. Cell. Cardiol., 1999, 931-947, 31(5).
Calder et al., Invest. Ophthalmol. Vis. Sci., 1999, 2019-2024, 40(9).
Caligan et al., Anal. Biochem., 2000, 36-44, 281(1).
Canataroglu et al., Ocul. Immunol. Inflamm., 2005, 375-381, 13(5).
Carter et al., Bio/Technology, 1992, 163-167, 10(2).
Casset et al., Biochem. Biophys. Res. Commun., 2003, 198-205, 307(1).
Cassidy et al., Br. J. Ophthamol., 1998, 181-185, 82(2).
Chae et al., J. Clin. Invest., 2004, 1082-1089, 114(8).
Champe et al., J. Biol. Chem., 1995, 1388-1394, 270(3).
Chan et al., Am. J. Respir. Cell Mol. Biol., 2000, 460-468, 22(4).
Chan et al., Biochemistry, 2000, 4838-4845, 39(16).
Chatterjee, Adv. Lip. Res., 1993, 25-48, 26.
Chatterjee, Arterioscler. Throm. Vasc. Biol., 1998, 1523-2533, 18(10).
Chatterjee, Chem. Phys. Lipids, 1999, 79-96, 102(1).
Chatterjee et al., Cancer Immunol. Immunother., 1994, 75-82, 38(2).
Chatterjee et al., J. Biol. Chem., 1999, 37407-37412, 274(52).
Chau et al., 221st ACS Natl. Mtg., San Diego, CA, USA, 2001, Am. Chem. Soc. (Abstract Only).
Chen et al., J. Mol. Biol., 1999, 865-881, 293(4).
Chothia et al., J. Mol. Biol., 1985, 651-663, 186(3).
Chothia et al., J. Mol. Biol., 1987, 901-917, 196(4).
Chun, Cult. Rev. Neuro., 1999, 151-168, 13(2) (Abstract Only).
Chun et al., Cell Biochem. Biophys., 1999, 213-242, 30(2).
Ciulla et al., Curr. Opin. Ophthalmol., 2001, 442-449, 12(6).
Clackson et al., Nature, 1991, 624-628, 352(6336).
Claus et al., Curr. Drug Targets, 2000, 185-205, 1(2).
Coderre et al., J. Neurosci., 1992, 3665-3670, 12(9).
Coligan et al.(Eds.), Current Protocols in Immunology vols. 1 and 2, 1991, Wiley-Interscience, New York, NY, USA (Table of Contents Only).
Cordis et al., J. Pharm. Biomed. Anal., 1998, 1189-1193, 16(7).
Cousins et al., Arch. Ophthalmol., 2004, 1013-1018, 122(7).
Cunningham et al., Science, 1989, 1081-1085, 244(4908).
Cuvlilier et al., Nature, 1996, 800-803, 381(6585).
Dart, Eye, 2003, 886-892, 17(8).
Das et al., Biochim. Biophys. Acta, 1984, 339-342, 777(2).
Davaille et al., J. Biol. Chem., 2000, 34268-34633, 275(44).
De Gruijl et al., Nat. Med., 1999, 1124-1125, 5(10).
De Pascalis et al., J. Immunol., 2002, 3076-3084, 169(6).
Denk et al., Curr. Eye Res., 2003, 35-44, 27(1).
Desgeorges et al., J. Rheumatol., 1997, 1510-1516, 24(8).
Desmouliere et al., J. Cell Biol., 1993, 103-111, 122(1).
Deutschman et al., Am. Heart J., 2003, 62-68, 146(1).
Di Girolamo et al., Invest. Ophthalmol. Vis. Sci., 2006, 2430-2437, 47(6).
Woolf et al., Pain, 1991, 293, 44(3).
Wright et al., Crit. Rev. Immunol., 1992, 125-168, 12(3-4).
Wu et al., J. Mol. Biol., 1999, 151-162, 294(1).
Xia et al., Proc. Natl. Acad. Sci. USA, 1988, 14196-14201, 95(24).

(56) References Cited

OTHER PUBLICATIONS

Xia et al., J. Biol. Chem., 1999, 33143-33147, 274(46).
Xia et al., Curr. Biol., 2000, 1527-1530, 10(23).
Xu et al., Cytokine, 1997, 1028-1033, 9(12).
Xu et al., J. Biol. Chem., 1998, 16521-16526, 273(26).
Xu et al., Nat. Cell Biol., 2000, 261-267, 2(5).
Yada et al., J. Biol. Chem., 1995, 12677-12684, 270(21).
Yamada et al., Eur. J. Biochem., 1988, 213-220, 175(2).
Yamagami et al., Mol Vis, 2005, 632-640, 11.
Yamaji et al., J. Biol. Chem., 1998, 5300-5306, 273(9).
Yamakage et al., J. Exp. Med., 1995, 1227-1234, 175(5).
Yamamoto et al., Am. J. Ophthal., 2001, 369-377, 132(3).
Yamanaka et al., J. Neurochem., 1982, 1753-1764, 38(6).
Yamanaka et al., J. Biol. Chem., 2004, 53994-54001, 279(52).
Yamazaki et al., Biochem. Biophys. Res. Commun., 2000, 583-589, 268(2).
Yanaga et al., FEBS Lett., 1992, 297-300, 314(3).
Yao et al., Ocul. Immunol. Inflamm., 2003, 211-222, 11(3).
Yatomi et al., Blood, 1995, 193-202, 86(1).
Yatomi et al., J. Biochem., 1997, 969-973, 121(5).
Yatomi et al., J. Biol. Chem., 1997, 5291-5297, 272(8).
Yellon et al., Cardiovasc. Res., 1992, 983-987, 26(10).
Yoshimura et al., J. Neurochem., 1999, 675-683, 73(2).
Yu et al., J. Mol. Neurosci., 2000, 85-97, 15(2).
Zager et al., Kidney Int., 1997, 942-952, 52(4).
Zapata et al., Protein Eng., 1995, 1057-1062, 8(10).
Zarbin, Arch. Ophthalmol., 2004, 598-614, 122(4).
Zechner et al., J. Biol. Chem., 1998, 8232-8239, 273(14).
Zelinski et al., J. Biol. Chem., 1980, 11423-11428, 255(23).
Zhang et al., J. Cell Biol., 1991, 155-167, 114(1).
Zhang et al., Blood, 1999, 2984-2990, 93(9).
Zhang et al., Gene, 1999, 89-99, 227(1).
Zhang et al., Mol. Genet. Metab., 2000, 301-309, 70(4).
Zhang et al., J. Phsyiol., 2002, 385-402, 544(2).
Zhang et al., Transplantation, 2003, 1511-1513, 76(10).
Zhang et al., J. Neurophysiol., 2006, 1042-1052, 96(3).
Zhang et al., J. Phsyiol., 2006, 101-113, 575(1).
Zheng et al., Jpn. J. Ophthalmol., 2003, 158-165, 47(2).
Zhou et al., Biochem. Biophys. Res. Comm., 1998, 502-507, 242(3).
Zhu et al., Arterioscler. Thromb. Vasc. Biol., 2002, 450-455, 22(3).
Zweerink et al., J. Biol. Chem., 1992, 25032-25038, 267(35).
Humpf et al., J. Biol. Chem., 1998, 19060-19064, 273(30).
Huwiler et al., Biochim. Biophys. Acta, 2000, 63-99, 1485(2-3).
Hwang et al., Proc. Natl. Acad. Sci. USA, 1980, 4030-4034, 77(7).
Igarashi, J. Biochem., 1997, 1080-1087, 122(6).
Igarashi, Ann. NY Acad. Sci.,1998, 19-31, 845.
Igarashi et al., Proc. Natl. Acad. Sci. USA, 2003, 10664-10669, 100(19).
Ikeda et al., Am J. Physiol. Gastrointest. Liver Physiol., 2000, G304-G310, 279(2).
Ikezawa et al., Biochim. Biophys. Acta, 1978, 247-256, 528(2).
Im et al., J. Biol. Chem., 2000, 14281-14286, 275(19).
Im et al., Mol. Pharmacol., 2000, 753-759, 57(4).
Ing et al., Ophthalmology, 1998, 1855-1865, 105(10).
Ishibashi et al., Arch. Ophthalmol., 1995, 227-231, 113(2).
Izuhara et al., Organic Lett., 2001, 1653-1656, 3(11).
Jakobovits et al., Nature, 1993, 255-258, 362(6417).
Jakobovits et al., Proc. Natl. Acad. Sci. USA,1993, 2551-2555, 90(6).
Jerdan et al., Ophthalmology, 1989, 801-810, 96(6).
Jester et al., Cornea, 1997, 177-187, 16(2).
Jester et al., Exp. Eye Res., 2003, 581-592, 77(5).
Jimbo et al., J. Biochem., 2000, 485-491, 127(3).
Jin et al., Exp. Neurol., 2008, 229-237, 210(1).
Jo et al., Am. J. Pathol., 2006, 2036-2053, 168(6).
Johansen et al., Nucl. Acids Res., 1998, 10370, 16(21).
Johnson et al., Exp. Eye Res., 2000, 441-449, 70(4).
Jolly et al., J. Exp. Med., 2004, 959-970, 199.
Jolly et al., Blood, 2005, 4736-4742, 105(12).
Jones et al., Nature, 1986, 522-525, 321(6069).
Jones et al., J. Neurosci., 2002, 2690-2700, 22(7).
Jonghe et al., Bioorg. Medicinal Chem. Lett., 1999, 3175-3180, 9(21).
Jordan et al., Cardiovasc. Res., 1999, 860-878, 43(4).
Joseph et al., Eur. J. Neurosci., 2004, 2896-2902, 20(11).
Joussen et al., FASEB J, 2003, 76-78, 17(1).
Kabat, Pharmacol. Rev., 1982, 23-38, 34(1).
Kajstura et al., Lab. Invest., 1996, 86-107, 74(1).
Kanfer et al., J. Biol. Chem., 1966, 1081-1084, 241(5).
Katircioglu et al., J. Cardiovasc. Surg. (Torino), 1999, 45-50, 41(1).
Kaur et al., Drug Dev. Ind. Pharm., 2002, 473-493, 28(5).
Kawasaki et al., Br. J. Ophthalmol., 2000, 1191-1193, 84(10).
Kay et al., Comb. Chem. High Throughput Screen, 2001, 535-543, 4(7) (Abstract Only).
Kent et al., Mol. Vis., 2003, 747-755, 9.
Kester, Trends Glycosci. Glycotechnol., 1997, 447-460, 9(50).
Kihara et al., Circ. Res., 1989, 1029-1044, 65(4).
Kim et al., J. Biol. Chem., 1991, 484-489, 266(1).
Kimura et al., J. Biol. Chem., 2001, 15208-15215, 276(18).
Kita et al., Biochim. Biophys. Acta, 2000, 111-120, 1485(2-3).
Klein et al., Science, 2005, 385-389, 308(5720).
Kohama et al., J. Biol. Chem., 1998, 23722-23728, 273(37).
Kohler et al., Nature, 1975, 495-497, 256(5517).
Kolesnick, Trends Biochem. Sci., 1999, 224-225, 24(6).
Kolesnick, J. Clin. Inv., 2002, 3-8, 110(1).
Kolesnick et al., J. Biol. Chem., 1990, 18803-18808, 265(31).
Gonzalez-Zorn et al., Mol. Microbial., 1999, 510-523, 33(3).
Gorin et al., Mol. Vis., 1999, 29-34, 5.
Gragoudas et al., N. Engl. J. Med., 2004, 2805-2816, 351(27).
Graham et al., J. Gen Virol., 1977, 59-72, 36(1).
Graler et al., Genomics, 1998, 164-169, 53(2).
Granziero et al., Eur. J. Immunol., 1999, 1127-1138, 29(4).
Grosskreutz et al., Microvasc. Res., 1999, 128-136, 58(2).
Grossniklaus et al., Ophthalmology, 1994, 1099-1111, 101(6).
Grossniklaus et al., Mol. Vis., 2002, 119-126, 8.
Gruber et al., J. Immunol., 1994, 5368-5374, 152(11).
Gryziewicz, Adv. Drug Deliv. Rev., 2005, 2092-2098, 57(14).
Gunther, Eur. J. Pharma., 2000, 123-126, 406(1).
Guo et al., Am. J. Pathol., 2003, 1083-1093, 162(4).
Gura, Science, 1997, 1041-1042, 278(5340).
Guss et al., EMBO J., 1986, 1567-1575, 5(7).
Hageman et al., Proc. Natl. Acad. Sci. USA, 2005, 7227-7232, 102(20).
Haimovitz-Friedman et al., J. Exp. Med., 1994, 525-535, 180(2).
Hakogi et al., Org. Lett., 2000, 2627-2629, 2(17).
Ham et al., Methods Enzmol., 1979, 44-93, 58.
Hama et al., J. Biol. Chem., 2004, 17634-17639, 279(17).
Hanada et al., Biochem. Pharmacol., 2000, 1211-1216, 59(10).
Hannun et al., Science, 1989, 500-507, 243(4890).
Hannun et al.., Adv. Lipid Res., 1993, 27-41, 25.
Hannun, Trends Biochem. Sci., 1995, 73-77, 20(2).
Hannun, Science, 1996, 1855-1859, 274(5294).
Hannun at al, Trends Cell Biol., 2000, 73-80, 10(2).
Harada et al., Prog. Retin. Eye Res., 2006, 149-164, 25(2).
Harris et al., Nat. Rev. Drug Disc., 2003, 214-221, 2(3).
He et al., Anal. Biochem., 1999, 264-269, 274(2).
Hegde et al., Transplantation, 2005, 23-31, 79(1).
Heringdorf et al., Eur. J. Pharmacol., 2001, 145-154, 414(2-3).
Hernandez et al., Circ. Res., 2000, 198-204, 86(2).
Hetland et al., Scand. J. Clin. Lab. Invest., 1982(57-61, 42(1).
Heymans et al., Am. J. Pathol., 2005, 15-25, 166(1).
Higuchi et al., J. Immunol., 1996, 297-304, 157(1).
Hinkovska-Glacheva et al., Blood, 1998, 4761-4769, 91(12).
Hise et al., J. Clin. Invest, 1986, 768-773, 77(3).
Hla et al., J. Biol. Chem., 1990, 9308-9313, 265(16).
Hla, Semin. Cell Dev. Biol., 2004, 513-520, 15(5).
Hofmann et al., Proc. Natl. Acad. Sci. USA, 2000, 5895-5900, 97(11).
Hofstadler et al., Anal. Chem., 1999, 3436-3440, 71(16).
Holliger et al., Proc. Natl. Acad. Sci. USA, 1993, 6444-6448, 90(14).
Holm et al., Mol. Immunol., 2007, 1075-1084, 44.
Holopainen et al., J Biol. Chem., 2000, 16484-16489, 275(22).
Hoogenboom et al., J. Mol. Biol., 1991, 381-388, 227(2).
Horn et al., J. Antibiot. (Tokyo), 1992, 1692-1696, 45(10).

(56) References Cited

OTHER PUBLICATIONS

Hoye et al., Organic Letts., 2000, 1481-1483, 2(10).
Hudson, Curr. Op. Biotechnol., 1999, 395-402, 9(4).
Hueber et al., Int. Ophthalmol., 1996, 345-350, 20(6).
Hughes et al., Invest. Ophthalmol. Vis. Sci., 2004, 2795-2806, 45(8).
Suomalainen et al., Am. J. Pathol., 2005, 773-781, 166(3).
Szulc et al., Tetrahedron Lett., 2000, 7821-7824, 41(41).
Takuwa, Biochim. Biophys. Acta, 2002, 112-120, 1582(1-3).
Tamura et al., J. Biochem. (Tokyo), 1992, 488-491, 112(4).
Tanaka et al., J. Am. Chem. Soc., 1997, 7871-7872, 199(33).
Tani et al., J. Biol. Chem., 2000, 3462-3468, 275(5).
Tazabekova et al., Bioorg. Khim., 1987, 648-653, 13(5) (English Abstract Only).
Tezel et al., Mol. Med., 2004, 417-420, 10(9).
Tomasek et al., Nat. Rev. Mol. Cell Biol., 2002, 349-363, 3(5).
Tomita et al.., J. Biochem. (Tokyo), 1990, 811-815, 108(5).
Tomiuk et al., Proc. Natl. Acad. Sci. USA, 1998, 3638-3643, 95(7).
Tonnetti et al., J. Exp. Med., 1999, 1581-1589, 189(10).
Torley et al., Anal. Biochem., 1994, 461-464, 222(2).
Tosaka et al., Stroke, 2001, 2913-2919, 32(12).
Trautmann et al., J. Pathol., 2000, 100-106, 190(1).
Triola et al., Angew. Chem. Int. Ed., 2001, 1960-1962, 40(10).
Tripathi et al., Exp. Eye Res., 1996, 339-346, 63(3).
Tsunoda et al., J. Biochem. Mol. Toxicol., 1998, 281-289, 12(5).
Tsutsumi et al., J. Leukoc. Biol., 2003, 25-32, 74(1).
Tutt et al., J. Immunol., 1991, 60-69, 147(1).
Uchida et al., J. Antibiot. (Tokyo), 1999, 572-574, 52(6).
Ueno et al., Invest. Ophthalmol. Vis. Sci., 2005, 4097-4106, 46(11).
Urata et al., Kobe J. Med. Sci., 2005, 17-27, 51(1).
Urdal, Dissertation Abstracts Int., 1980, 4062-4063, 41(11B) (Abstract Only).
Urlaub et al., Proc. Natl. Acad. Sci. USA, 1980, 4216-4220, 77(7).
Usia et al., Biochemistry, 2000, 9657-9668, 40(32).
Usui et al., J. Biol. Chem., 2004, 12300-12311, 279(13).
Vadas et al., Circ. Res., 1996, 1216-1217, 79(6).
Vajdos et al., J. Mol. Biol., 2002, 415-428, 320(2).
Van Brocklyn et al., J. Cell Biol., 1998, 229-240, 142(1).
Van Brocklyn et al., J. Biol. Chem., 1999, 4626-4632, 274(8).
Van Den Brink et al., Blood, 2002,2828-2834, 99(8).
Van Veldhoven, Methods Enzymol., 1999, 244-254, 311.
Van Veldhoven et al., Adv. Lipid Res., 1993, 69-98, 26.
Van Veldhoven et al., Biochim. Biophys. Acta, 2000, 128-134, 1487(2-3).
Van Wijngaarden et al., JAMA, 2005, 1509-1513, 293(12).
Verma et al., Curr. Eye Res., 1997, 1202-1208, 16(12).
Vidinova et al., Klin. Monatsbl. Augenheilkd., 2005, 568-571, 222(7) (English Abstract Only).
Vine et al., Ophthalmology, 2005, pp. 2076-2080, 112(12).
Virag et al., Am. J. Pathol., 2003, 2433-2440, 163(6).
Visentin et al., Cancer Cell, 2006, 225-238, 9(3).
Vivekananda et al., Am. J. Physiol. Lung Cell. Mol. Physiol., 2001, L98-L107, 228(1).
Walev et al., Infect. Immun., 1996, 2974-2979, 64(8).
Wang et al., J. Biol. Chem., 1999, 35343-35350, 274(50).
Wang et al., J. Biol. Chem., 2001, 49213-49220, 276(52).
Webb et al., J. Neuroimmunol., 2004, 108-121, 153(1-2).
Webster's Dictionary, 1990, p. 1135.
Wilkinsin et al., in Wilkinsin et al., Ed., Michel's Retinal Detachment 2nd Edition, Mosby, Inc., St Louis, 1997, 641-771, Ch. 12.
Winter et al., Annu. Rev. Immunol., 1994, 433-455, 12.
Witmer et al., Prog. Retin. Eye Res., 2003, 1-29, 22(1).
Saika et al., Am. J. Pathol., 2006, 1848-1860, 168(6).
Saint-Joanis et al., Mol. Gen. Genet., 1989, 453-460, 219(3).
Saishin et al., J. Cell. Physiol., 2003, 241-248, 195(2).
Saito et al., Organic Letts, 2000, 505-506, 2(4).
Sakai et al., Jpn J. Pharmacol., 1978, 223-229, 28(2).
Sato, J. Clin. Invest., 2000, 939-940, 106(8).
Sawada et al., Cell Death Differ., 2000, 761-772, 7(9).
Sawai et al., J. Biol. Chem., 1999, 38131-38139, 274(53).
Sawai et al., J. Biol. Chem., 2000, 39793-39798, 275(50).
Schissel et al., J. Biol. Chem., 1996, 18431-18436, 271(31).
Schottenfeld et al., CA Cancer J. Clin., 2006, 69-83, 56(2).
Seddon et al., Int. Ophthalmol. Clin., 2004, 17-39, 44(4).
Sedlakova et al., Transplantation, 2005, 297-303, 79(3).
Segui et al., J. Clin. Invest., 2001, 143-151, 108(1).
Sergeyev et al., Kosm. Biol. Aviakosm. Med. (Russian), 1981, 71-74, 15(6) (English Translation 104-108).
Shalaby et al., J. Exp. Med., 1992, 217-225, 175(1).
Shaunak et al., Nat. Chem. Biol., 2006, 312-313, 2(6).
Shayman et al., Methods Enzymol., 1999, 42-49, 311.
Shayman et al., Methods Enzymol., 1999, 373-387, 311.
Shinghal et al., J. Neurochem., 1993, 2279-2285, 61(6).
Siehler et al., J. Biol. Chem., 2001, 48733-48739, 276(52).
Siess et al., IUBMB Life, 2000, 161-171, 49(3).
Sivalingam et al., Arch. Ophthalmol., 1990, 869-872, 108(6).
Skolnick et al., Trends Biotechnol., 2000, 34-39, 18.
Smith et al., Am. Heart J., 1982, 716-723, 103(4, Pt. 2).
Smith et al., Toxicol. Sci., 2000, 240-249, 56(1).
Snow et al., Eur. J. Immunol., 1998, 3354-3361, 28(10).
Sotozono et al., Curr. Eye Res., 1997, 670-676, 19.
Spann et al., Eur. J. Immunol., 1999, 4060-4071, 29(12).
Spaide, Am. J. Ophthalmol., 2006, 149-156, 141(1).
Spence, Adv. Lipid Res., 1993, 3-23, 26.
Spence et al., J. Biol. Chem., 1989, 5358-5363, 264(10).
Spiegel et al., FASEB J., 1996, 1388-1397, 10(12).
Spiegel et al., Differentiation, and Death, Biochemistry (Mosc)., 1998, 69-73, 63(1).
Spiegel et al., Biochim. Biophys. Acta, 2000, 107-116, 1484(2-3).
Spiegel et al., Leukemia, 2002, 1596-1602, 16(9).
Spiegel et al., Nat. Rev. Mol. Cell Biol., 2003, 397-407, 4(5).
Squires et al., J. Mol. Cell. Cardiol., 2005, 599-707, 39(4).
Staton et al., Int. J. Exp. Pathol., 2004, 233-248, 85(5).
Stavri et al., Circulation, 1995, 11-14, 92(1).
Stramer et al., Invest. Ophthalmol. Vis. Sci., 2003, 4237-4246, 44(10).
Strom et al., Invest. Ophthalmol. Vis. Sci., 2005, 3855-3858, 46(10).
Su et al., J. Biol. Chem., 1994, 16512-16517, 269(23).
Sucheck et al., Curr. Opin. Drug Disc. Develop., 2001, 462-470, 4(4) (Abstract Only).
Sugita at al, Biochim. Biophys. Acta, 1975, 125-131, 398(1).
Sugiyama et al., Cardiovasc. Res., 2000, 119-125, 46(1).
Sultana et al., Curr. Drug Deliv., 2006, 207-217, 3(2).
Sumnicht et al., Arch. Biochem. Biophys., 1982, 628-637, 215(2).
Sun et al., Cardiovasc. Res., 2000, 250-256, 46(2).
Sun et al., J. Mol. Cell. Cardiol., 1996, 851-858, 28(5).

PREVENTION AND TREATMENT OF PAIN USING ANTIBODIES TO SPHINGOSINE-1-PHOSPHATE

RELATED APPLICATIONS

This application is a continuation-in-part of, and claims the benefit of and priority to, U.S. non-provisional patent application Ser. No. 12/258,383, filed on 24 Oct. 2008 and issued on 27 Sep. 2011 as U.S. Pat. No. 8,026,342, the contents of each of which are herein incorporated by reference in its entirety for any and all purposes.

BACKGROUND OF THE INVENTION

1. Field of the Invention

The present invention relates to agents that bind sphingosine-1-phosphate (S1P), particularly to humanized monoclonal antibodies, antibody fragments, and antibody derivatives specifically reactive to S1P under physiological conditions. Such agents can be used in the treatment and/or prevention of various diseases or conditions through the delivery of pharmaceutical compositions that contain such agents.

The following description includes information that may be useful in understanding the present invention. It is not an admission that any of the information provided herein, or any publication specifically or implicitly referenced herein, is prior art, or even particularly relevant, to the presently claimed invention.

2. Background.

Bioactive Signaling Lipids

Lipids and their derivatives are now recognized as important targets for medical research, not as just simple structural elements in cell membranes or as a source of energy for β-oxidation, glycolysis or other metabolic processes. In particular, certain bioactive lipids function as signaling mediators important in animal and human disease. Although most of the lipids of the plasma membrane play an exclusively structural role, a small proportion of them are involved in relaying extracellular stimuli into cells. "Lipid signaling" refers to any of a number of cellular signal transduction pathways that use cell membrane lipids as second messengers, as well as referring to direct interaction of a lipid signaling molecule with its own specific receptor. Lipid signaling pathways are activated by a variety of extracellular stimuli, ranging from growth factors to inflammatory cytokines, and regulate cell fate decisions such as apoptosis, differentiation and proliferation. Research into bioactive lipid signaling is an area of intense scientific investigation as more and more bioactive lipids are identified and their actions characterized.

Examples of bioactive lipids include the eicosanoids (including the cannabinoids, leukotrienes, prostaglandins, lipoxins, epoxyeicosatrienoic acids, and isoeicosanoids), non-eicosanoid cannabinoid mediators, phospholipids and their derivatives such as phosphatidic acid (PA) and phosphatidylglycerol (PG), platelet activating factor (PAF) and cardiolipins as well as lysophospholipids such as lysophosphatidyl choline (LPC) and various lysophosphatidic acids (LPA). Bioactive signaling lipid mediators also include the sphingolipids such as sphingomyelin, ceramide, ceramide-1-phosphate, sphingosine, sphingosylphosphoryl choline, sphinganine, sphinganine-1-phosphate (Dihydro-S1P) and sphingosine-1-phosphate. Sphingolipids and their derivatives represent a group of extracellular and intracellular signaling molecules with pleiotropic effects on important cellular processes. Other examples of bioactive signaling lipids include phosphatidylserine (PS), phosphatidylinositol (PI), phosphatidylethanolamine (PEA), diacylglyceride (DG), sulfatides, gangliosides, and cerebrosides.

Sphingolipids are a unique class of lipids that were named, due to their initially mysterious nature, after the Sphinx Sphingolipids were initially characterized as primary structural components of cell membranes, but recent studies indicate that sphingolipids also serve as cellular signaling and regulatory molecules (Hannun, et al., Adv. Lipid Res. 25:27-41, 1993; Speigel, et al., FASEB J. 10:1388-1397, 1996; Igarashi, J. Biochem 122:1080-1087, 1997; Hla, T. (2004). *Semin Cell Dev Biol,* 15, 513-2; Gardell, S. E., Dubin, A. E. & Chun, J. (2006). *Trends Mol Med,* 12, 65-75). Sphingolipids are primary structural components of cell membranes that also serve as cellular signaling and regulatory molecules (Hannun and Bell, Adv. Lipid Res. 25: 27-41, 1993; Igarashi, J. Biochem 122: 1080-1087, 1997). The sphingolipid signaling mediators, ceramide (CER), sphingosine (SPH) and sphingosine-1-phosphate (S1P), have been most widely studied and have recently been appreciated for their roles in the cardiovascular system, angiogenesis and tumor biology (Claus, et al., Curr Drug Targets 1: 185-205, 2000; Levade, et al., Circ. Res. 89: 957-968, 2001; Wang, et al., J. Biol. Chem. 274: 35343-50, 1999; Wascholowski and Giannis, Drug News Perspect. 14: 581-90, 2001; Spiegel, S. & Milstien, S. (2003). Sphingosine-1-phosphate: an enigmatic signaling lipid. *Nat Rev Mol Cell Biol,* 4, 397-407).

For a review of sphingolipid metabolism, see Liu, et al., Crit. Rev. Clin. Lab. Sci. 36:511-573, 1999. For reviews of the sphingomyelin signaling pathway, see Hannun, et al., Adv. Lipid Res. 25:27-41, 1993; Liu, et al., Crit. Rev. Clin. Lab. Sci. 36:511-573, 1999; Igarashi, J. Biochem. 122:1080-1087, 1997; Oral, et al., J. Biol. Chem. 272:4836-4842, 1997; and Spiegel et al., Biochemistry (Moscow) 63:69-83, 1998.

S1P is a mediator of cell proliferation and protects from apoptosis through the activation of survival pathways (Maceyka, et al. (2002), BBA, vol. 1585): 192-201, and Spiegel, et al. (2003), Nature Reviews Molecular Cell Biology, vol. 4: 397-407). It has been proposed that the balance between CER/SPH levels and S1P provides a rheostat mechanism that decides whether a cell is directed into the death pathway or is protected from apoptosis. The key regulatory enzyme of the rheostat mechanism is sphingosine kinase (SPHK) whose role is to convert the death-promoting bioactive signaling lipids (CER/SPH) into the growth-promoting S1P. S1P has two fates: S1P can be degraded by S1P lyase, an enzyme that cleaves S1P to phosphoethanolamine and hexadecanal, or, less common, hydrolyzed by S1P phosphatase to SPH.

The pleiotropic biological activities of S1P are mediated via a family of G protein-coupled receptors (GPCRs) originally known as Endothelial Differentiation Genes (EDG). Five GPCRs have been identified as high-affinity S1P receptors (S1PRs): $S1P_1$/EDG-1, $S1P_2$/EDG-5, $S1P_3$/EDG-3, $S1P_4$/EDG-6, and $S1P_5$/EDG-8 only identified as late as 1998 (Lee, et al., 1998). Many responses evoked by S1P are coupled to different heterotrimeric G proteins ($G_{q-}$, $G_i$, $G_{12-13}$) and the small GTPases of the Rho family (Gardell, et al., 2006).

In the adult, S1P is released from platelets (Murata et al., 2000) and mast cells to create a local pulse of free S1P (sufficient enough to exceed the $K_d$ of the S1PRs) for promoting wound healing and participating in the inflammatory response. Under normal conditions, the total S1P in the plasma is quite high (300-500 nM); however, it has been hypothesized that most of the S1P may be 'buffered' by serum proteins, particularly lipoproteins (e.g., HDL>LDL>VLDL) and albumin, so that the bio-available S1P (or the free fraction of S1P) is not sufficient to appreciably activate S1PRs (Murata et al., 2000). If this were not the case, inappropriate angiogenesis and inflammation would result. Intracellular actions of S1P have also been suggested (see, e.g., Spiegel S, Kolesnick R (2002), Leukemia, vol. 16: 1596-602; Suomalainen, et at (2005), Am J Pathol, vol. 166: 773-81).

Widespread expression of the cell surface S1P receptors allows S1P to influence a diverse spectrum of cellular responses, including proliferation, adhesion, contraction, motility, morphogenesis, differentiation, and survival. This spectrum of response appears to depend upon the overlapping or distinct expression patterns of the S1P receptors within the cell and tissue systems. In addition, crosstalk between S1P and growth factor signaling pathways, including platelet-derived growth factor (PDGF), vascular endothelial growth factor (VEGF), and basic fibroblastic growth factor (bFGF), have recently been demonstrated (see, e.g., Baudhuin, et al. (2004), FASEB J, vol. 18: 341-3). The regulation of various cellular processes involving S1P has particular impact on neuronal signaling, vascular tone, wound healing, immune cell trafficking, reproduction, and cardiovascular function, among others. Alterations of endogenous levels of S1P within these systems can have detrimental effects, eliciting several pathophysiological conditions, including cancer, inflammation, angiogenesis, heart disease, asthma, and autoimmune diseases.

A recent novel approach to the treatment of various diseases and disorders, including cardiovascular diseases, cerebrovascular diseases, and various cancers, involves reducing levels of biologically available S1P, either alone or in combination with other treatments. While sphingolipid-based treatment strategies that target key enzymes of the sphingolipid metabolic pathway, such as SPHK, have been proposed, interference with the lipid mediator S1P itself has not until recently been emphasized, largely because of difficulties in directly mitigating this lipid target, in particular because of the difficulty first in raising and then in detecting antibodies against the S1P target.

Recently, the generation of antibodies specific for S1P has been described. See, e.g., commonly owned, U.S. patent application Ser. No. 20070148168; WO2007/053447. Such antibodies, which can, for example, selectively adsorb S1P from serum, act as molecular sponges to neutralize extracellular S1P. See also commonly owned U.S. Pat. Nos. 6,881, 546 and 6,858,383 and U.S. patent application Ser. No. 10/029,372. SPHINGOMAB™, the murine monoclonal antibody (mAb) developed by Lpath, Inc. and described in certain patents or patent applications listed above, has been shown to be effective in models of human disease. In some situations, a humanized antibody may be preferable to a murine antibody, particularly for therapeutic uses in humans, where human-anti-mouse antibody (HAMA) response may occur. Such a response may reduce the effectiveness of the antibody by neutralizing the binding activity and/or by rapidly clearing the antibody from circulation in the body. The HAMA response can also cause toxicities with subsequent administrations of mouse antibodies.

A humanized anti-S1P antibody has been developed by Lpath, Inc. This antibody has all the advantages of the murine mAb in terms of efficacy in binding S1P, neutralizing S1P and modulating disease states related to S1P, but with none of the potential disadvantages of the murine mAb when used in a human context. As described in the examples hereinbelow, this humanized antibody (referred to as LT1009 or sonepcizumab) has in fact shown activity greater than that of the parent (murine) antibody in animal models of disease.

3. Definitions

Before describing the instant invention in detail, several terms used in the context of the present invention will be defined. In addition to these terms, others are defined elsewhere in the specification, as necessary. Unless otherwise expressly defined herein, terms of art used in this specification will have their art-recognized meanings. In the event of conflict, the present specification, including definitions, will control.

An "immune-derived moiety" includes any antibody (Ab) or immunoglobulin (Ig), and refers to any form of a peptide, polypeptide derived from, modeled after or encoded by, an immunoglobulin gene, or a fragment of such peptide or polypeptide that is capable of binding an antigen or epitope (see, e.g., Immunobiology, 5th Edition, Janeway, Travers, Walport, Shlomchiked. (editors), Garland Publishing (2001)). In the present invention, the antigen is a bioactive lipid molecule.

An "anti-S1P antibody" or an "immune-derived moiety reactive against S1P" refers to any antibody or antibody-derived molecule that binds S1P. As will be understood from these definitions, antibodies or immune-derived moieties may be polyclonal or monoclonal and may be generated through a variety of means, and/or may be isolated from an animal, including a human subject.

A "bioactive lipid" refers to a lipid signaling molecule. In general, a bioactive lipid does not reside in a biological membrane when it exerts its signaling effects, which is to say that while such a lipid species may exist at some point in a biological membrane (for example, a cell membrane, a membrane of a cell organelle, etc.), when associated with a biological membrane it is not a "bioactive lipid" but is instead a "structural lipid" molecule. Bioactive lipids are distinguished from structural lipids (e.g., membrane-bound phospholipids) in that they mediate extracellular and/or intracellular signaling and thus are involved in controlling the function of many types of cells by modulating differentiation, migration, proliferation, secretion, survival, and other processes. In vivo, bioactive lipids can be found in extracellular fluids, where they can be complexed with other molecules, for example serum proteins such as albumin and lipoproteins, or in "free" form, i.e., not complexed with another molecule species. As extracellular mediators, some bioactive lipids alter cell signaling by activating membrane-bound ion channels or G-protein coupled receptors that, in turn, activate complex signaling systems that result in changes in cell function or survival. As intracellular mediators, bioactive lipids can exert their actions by directly interacting with intracellular components such as enzymes and ion channels. Representative examples of bioactive lipids include LPA and S1P.

The term "therapeutic agent" means an agent to mitigate angiogenesis and/or neovascularization, e.g., CNV and BV maturation, edema, vascular permeability and fibrosis, fibrogenesis and scarring associated with, or part of the underlying pathology of, ocular diseases and conditions.

The term "combination therapy" refers to a therapeutic regimen that involves the provision of at least two distinct therapies to achieve an indicated therapeutic effect. For example, a combination therapy may involve the administration of two or more chemically distinct active ingredients, for example, an anti-LPA antibody and an anti-S1P antibody. Alternatively, a combination therapy may involve the administration of an immune-derived moiety reactive against a bioactive lipid and the administration of one or more other medicaments, such as pain relief agents. Combination therapy may, alternatively, involve administration of an anti-lipid antibody together with the delivery of another treatment, such as radiation therapy and/or surgery. Further, a combination therapy may involve administration of an anti-lipid antibody together with one or more other biological agents (e.g., anti-VEGF, TGFβ, PDGF, or bFGF agent), other medicaments and another treatment such as radiation and/or surgery. In the context of combination therapy using two or more chemically distinct active ingredients, it is understood that the active ingredients may be administered as part of the same composition or as different compositions. When administered as separate compositions, the compositions comprising the different active ingredients may be administered at the same or different times, by the same or different routes, using the same of different dosing regimens, all as the particular context requires and as determined by the attending physician. Similarly, when one or more anti-lipid antibody species, for example, an anti-S1P antibody, alone or in conjunction with one or more medicaments are combined with, for example, radiation and/or surgery, the drug(s) may be delivered before or after surgery or radiation treatment.

An "anti-S1P agent" refers to any agent that is specifically reactive to S1P, and includes antibodies or antibody-derived molecules or non-antibody-derived moieties that bind S1P and its variants.

A "hapten" refers to a molecule adapted for conjugation to a hapten, thereby rendering the hapten immunogenic. A representative, non-limiting class of hapten molecules is proteins, examples of which include albumin, keyhole limpet hemocyanin, hemaglutanin, tetanus, and diphtheria toxoid. Other classes and examples of hapten molecules suitable for use in accordance with the invention are known in the art. These, as well as later discovered or invented naturally occurring or synthetic haptens, can be adapted for application in accordance with the invention.

The term "chemotherapeutic agent" means anti-cancer and other anti-hyperproliferative agents. Put simply, a "chemotherapeutic agent" refers to a chemical intended to destroy cells and tissues. Such agents include, but are not limited to: (1) DNA damaging agents and agents that inhibit DNA synthesis: e.g., anthracyclines (e.g., doxorubicin, donorubicin, epirubicin), alkylating agents (e.g., bendamustine, busulfan, carboplatin, carmustine, cisplatin, chlorambucil, cyclophosphamide, dacarbazine, hexamethylmelamine, ifosphamide, lomustine, mechlorethamine, melphalan, mitotane, mytomycin, pipobroman, procarbazine, streptozocin, thiotepa, and triethylenemelamine), platinum derivatives (e.g., cisplatin, carboplatin, cis diamminedichloroplatinum), telomerase and topoisomerase inhibitors (e.g., Camptosar), (2) tubulin-depolymerizing agents: e.g., taxoids (e.g., Paclitaxel, docetaxel, BAY 59-8862), (3) anti-metabolites such as capecitabine, chlorodeoxyadenosine, cytarabine (and its activated form, ara-CMP), cytosine arabinoside, dacabazine, floxuridine, fludarabine, 5-fluorouracil, 5-DFUR, gemcitibine, hydroxyurea, 6-mercaptopurine, methotrexate, pentostatin, trimetrexate, and 6-thioguanine (4) anti-angiogenics (e.g., Avastin, thalidomide, revlimid, sunitinib, lenalidomide), vascular disrupting agents (e.g., flavonoids/flavones, DMXAA, combretastatin derivatives such as CA4DP, ZD6126, AVE8062A, etc.), (5) biologics such as antibodies or antibody fragments (e.g., Herceptin, Avastin, Panorex, Rituxan, Zevalin, Mylotarg, Campath, Bexar, Erbitux, Lucentis), and (6) endocrine therapy: e.g., aromatase inhibitors (e.g., 4-hydroandrostendione, exemestane, aminoglutehimide, anastrozole, letozole), anti-estrogens (e.g., Tamoxifen, Toremifine, Raoxifene, Faslodex), steroids such as dexamethasone, (7) immunomodulators: e.g., cytokines such as IFN-beta and IL2), inhibitors to integrins, other adhesion proteins and matrix metalloproteinases), (8) histone deacetylase inhibitors, (9) inhibitors of signal transduction such as inhibitors of tyrosine kinases like imatinib (Gleevec), (10) inhibitors of heat shock proteins, (11) retinoids such as all trans retinoic acid, (12) inhibitors of growth factor receptors or the growth factors themselves, (13) anti-mitotic compounds such as navelbine, Paclitaxel, taxotere, vinblastine, vincristine, vindesine, and vinorelbine, (14) anti-inflammatories such as COX inhibitors and (15) cell cycle regulators, e.g., check point regulators and telomerase inhibitors.

The term "sphingolipid" as used herein refers to the class of compounds in the art known as sphingolipids, including, but not limited to the following compounds (see http//www.lipidmaps.org as the site containing the links indicated by the bracketed alphanumeric strings below, which links contain chemical formulas, structural information, etc. for the corresponding compounds):

Sphingoid bases [SP01]
  Sphing-4-enines (Sphingosines) [SP0101]
  Sphinganines [SP0102]
  4-Hydroxysphinganines (Phytosphingosines) [SP0103]
  Sphingoid base homologs and variants [SP0104]
  Sphingoid base 1-phosphates [SP0105]
  Lysosphingomyelins and lysoglycosphingolipids [SP0106]
  N-methylated sphingoid bases [SP0107]
  Sphingoid base analogs [SP0108]
Ceramides [SP02]
  N-acylsphingosines (ceramides) [SP0201]
  N-acylsphinganines (dihydroceramides) [SP0202]
  N-acyl-4-hydroxysphinganines (phytoceramides) [SP0203]
  Acylceramides [SP0204]
  Ceramide 1-phosphates [SP0205]
Phosphosphingolipids [SP03]
  Ceramide phosphocholines (sphingomyelins) [SP0301]
  Ceramide phosphoethanolamines [SP0302]
  Ceramide phosphoinositols [SP0303]
Phosphonosphingolipids [SP04]
Neutral glycosphingolipids [SP05]
  Simple Glc series (GlcCer, LacCer, etc) [SP0501]
  GalNAcb1-3Gala1-4Galb1-4Glc- (Globo series) [SP0502]
  GalNAcb1-4Galb1-4Glc- (Ganglio series) [SP0503]
  Galb1-3GlcNAcb1-3Galb1-4Glc- (Lacto series) [SP0504]
  Galb1-4GlcNAcb1-3Galb1-4Glc- (Neolacto series) [SP0505]
  GalNAcb1-3Gala1-3Galb1-4Glc- (Isoglobo series) [SP0506]
  GlcNAcb1-2Mana1-3Manb1-4Glc- (Mollu series) [SP0507]
  GalNAcb1-4GlcNAcb1-3Manb1-4Glc- (Arthro series) [SP0508]
  Gal- (Gala series) [SP0509]
  Other [SP0510]
Acidic glycosphingolipids [SP06]
  Gangliosides [SP0601]
  Sulfoglycosphingolipids (sulfatides) [SP0602]
  Glucuronosphingolipids [SP0603]
  Phosphoglycosphingolipids [SP0604]
  Other [SP0600]
Basic glycosphingolipids [SP07]
Amphoteric glycosphingolipids [SP08]
Arsenosphingolipids [SP09]

The present invention provides anti-sphingolipid S1P agents that are useful for treating or preventing hyperproliferative disorders such as cancer and cardiovascular or cerebrovascular diseases and disorders and various ocular disorders, as described in greater detail below. In particular the invention is drawn to S1P and its variants including but are not limited to sphingosine-1-phosphate [sphingene-1-phosphate; D-erythro-sphingosine-1-phosphate; sphing-4-enine-1-phosphate; (E,2S,3R)-2-amino-3-hydroxy-octadec-4-enoxy] phosphonic acid (AS 26993-30-6), DHS1P is defined as dihydrosphingosine-1-phosphate [sphinganine-1-phosphate; [(2S,3R)-2-amino-3-hydroxy-octadecoxy]phosphonic acid; D-Erythro-dihydro-D-sphingosine-1-phosphate (CAS 19794-97-9]; SPC is sphingosylphosphoryl choline, lysosphingomyelin, sphingosylphosphocholine, sphingosine phosphorylcholine, ethanaminium; 2-((((2-amino-3-hydroxy-4-octadecenyl) oxy)hydroxyphosphinyl)oxy)-N,N,N-trimethyl-, chloride, (R-(R*,S*-(E))), 2-[[(E,2R,3S)-2-amino-3-hydroxy-octadec-4-enoxy]-hydroxy-phosphoryl] oxyethy 1-trimethyl-azanium chloride (CAS 10216-23-6).

The term "epitope" or "antigenic determinant" when used herein, unless indicated otherwise, refers to the region of S1P to which an anti-S1P agent is reactive to.

The term "hyperproliferative disorder" refers to diseases and disorders associated with, the uncontrolled proliferation cells, including but not limited to uncontrolled growth of organ and tissue cells resulting in cancers or neoplasia and benign tumors. Hyperproliferative disorders associated with endothelial cells can result in diseases of angiogenesis such as angiomas, endometriosis, obesity, age-related macular degeneration and various retinopathies, as well as the proliferation of endothelial cells and smooth muscle cells that cause restenosis as a consequence of stenting in the treatment of atherosclerosis. Hyperproliferative disorders involving fibroblasts (for example, fibrogenesis) include but are not limited to disorders of excessive scarring (for example, fibrosis) such as age-related macular degeneration, cardiac remodeling and failure associated with myocardial infarction, excessive wound healing such as commonly occurs as a consequence of surgery or injury, keloids, and fibroid tumors and stenting.

The compositions of the invention are used in methods of sphingolipid-based therapy. "Therapy" refers to the prevention and/or treatment of diseases, disorders or physical trauma.

The term "sphingolipid metabolite" refers to a compound from which a sphingolipid is made, as well as a that results from the degradation of a particular sphingolipid. In other words, a "sphingolipid metabolite" is a compound that is involved in the sphingolipid metabolic pathways. Metabolites include metabolic precursors and metabolic products. The term "metabolic precursors" refers to compounds from which sphingolipids are made. Metabolic precursors of particular interest include but are not limited to SPC, sphingomyelin, dihydrosphingosine, dihydroceramide, and 3-ketosphinganine. The term "metabolic products" refers to compounds that result from the degradation of sphingolipids, such as phosphorylcholine (e.g., phosphocholine, choline phosphate), fatty acids, including free fatty acids, and hexadecanal (e.g., palmitaldehyde).

As used herein, the term "therapeutic" encompasses the fill spectrum of treatments for a disease or disorder. A "therapeutic" agent of the invention may act in a manner that is prophylactic or preventive, including those that incorporate procedures designed to target individuals that can be identified as being at risk (pharmacogenetics); or in a manner that is ameliorative or curative in nature; or may act to slow the rate or extent of the progression of at least one symptom of a disease or disorder being treated; or may act to minimize the time required, the occurrence or extent of any discomfort or pain, or physical limitations associated with recuperation from a disease, disorder or physical trauma; or may be used as an adjuvant to other therapies and treatments.

"Treatment" refers to both therapeutic treatment and prophylactic or preventative measures. Those in need of treatment include those already with the disorder as well as those in which the disorder is to be prevented.

The term "combination therapy" refers to a therapeutic regimen that involves the provision of at least two distinct therapies to achieve an indicated therapeutic effect. For example, a combination therapy may involve the administration of two or more chemically distinct active ingredients, for example, a fast-acting chemotherapeutic agent and an anti-lipid antibody. Alternatively, a combination therapy may involve the administration of an anti-lipid antibody and/or one or more chemotherapeutic agents, alone or together with the delivery of another treatment, such as radiation therapy and/or surgery. Further, a combination therapy may involve administration of an anti-lipid antibody together with one or more other biological agents (e.g., anti-VEGF, TGFβ, PDGF, or bFGF agent), chemotherapeutic agents and another treatment such as radiation and/or surgery. In the context of the administration of two or more chemically distinct active ingredients, it is understood that the active ingredients may be administered as part of the same composition or as different compositions. When administered as separate compositions, the compositions comprising the different active ingredients may be administered at the same or different times, by the same or different routes, using the same of different dosing regimens, all as the particular context requires and as determined by the attending physician. Similarly, when one or more anti-lipid antibody species, for example, an anti-S1P antibody, alone or in conjunction with one or more chemotherapeutic agents are combined with, for example, radiation and/or surgery, the drug(s) may be delivered before or after surgery or radiation treatment.

"Monotherapy" refers to a treatment regimen based on the delivery of one therapeutically effective compound, whether administered as a single dose or several doses over time.

"Neoplasia" or "cancer" refers to abnormal and uncontrolled cell growth. A "neoplasm", or tumor or cancer, is an abnormal, unregulated, and disorganized proliferation of cell growth, and is generally referred to as cancer. A neoplasm may be benign or malignant. A neoplasm is malignant, or cancerous, if it has properties of destructive growth, invasiveness, and metastasis. Invasiveness refers to the local spread of a neoplasm by infiltration or destruction of surrounding tissue, typically breaking through the basal laminas that define the boundaries of the tissues, thereby often entering the body's circulatory system. Metastasis typically refers to the dissemination of tumor cells by lymphatics or blood vessels. Metastasis also refers to the migration of tumor cells by direct extension through serous cavities, or subarachnoid or other spaces. Through the process of metastasis, tumor cell migration to other areas of the body establishes neoplasms in areas away from the site of initial appearance.

"Mammal" for purposes of treatment refers to any animal classified as a mammal, including humans, domestic and farm animals, and zoo, sports, or pet animals, such as dogs, horses, cats, cows, etc. Preferably, the mammal is human.

"Native antibodies" and "native immunoglobulins" are usually heterotetrameric glycoproteins of about 150,000 Daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "variable" region comprises framework and CDRs (otherwise known as hypervariables) and refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework region (FR). The variable domains of native heavy and light chains each comprise four FRs (FR1, FR2, FR3 and FR4, respectively), largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat, et al., Sequences of Proteins of Immunological Interest, 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen binding. The hypervariable region comprises amino acid residues from a "complementarity determining region" or "CDR" (for example, residues 24-34 (L1), 50-56 (L2), and 89-97 (L3) in the light chain variable domain and 31-35 (H1), 50-65 (H2), and 95-102 (H3) in the heavy chain variable domain; Kabat, et al. (1991), above) and/or those residues from a "hypervariable loop" (for example residues 26-32 (L1), 50-52 (L2), and 91-96 (L3) in the light chain variable domain and 26-32 (H1), 53-55 (H2), and 96-101 (H3) in the heavy chain variable domain; Chothia and Lesk J. Mol. Biol. 196:901-917 (1987)). "Framework" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment that contains a complete antigen-recognition and -binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. Presently there are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The term "antibody" herein is used in the broadest sense and specifically covers monoclonal antibodies (including full length monoclonal antibodies), polyclonal antibodies, multispecific antibodies (e.g., bispecific antibodies), antibody fragments, and binding agents that employ the CDRs (or variant thereof that retain antigen binding activity) of the parent antibody. Antibodies are defined herein as retaining at least one desired activity of the parent antibody. Desired activities can include the ability to bind the antigen specifically, the ability to inhibit proleration in vitro, the ability to inhibit angiogenesis in vivo, and the ability to alter cytokine profile in vitro. "Antibody fragments" comprise a portion of a full-length antibody, generally the antigen binding or variable domain thereof. Examples of antibody fragments include Fab, Fab', F(ab')$_2$, and Fv fragments; diabodies; linear antibodies; single-chain antibody molecules; and multispecific antibodies formed from antibody fragments.

The term "monoclonal antibody" as used herein refers to an antibody obtained from a population of substantially homogeneous antibodies, for example, the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler, et al., Nature 256:495 (1975), or may be made by recombinant DNA methods (see, e.g., U.S. Pat. No. 4,816,567). The "monoclonal antibodies" may also be isolated from phage antibody libraries using the techniques described in Clackson, et al., Nature 352:624-628 (1991) and Marks et al., J. Mol. Biol. 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison, et al., Proc. Natl. Acad. Sci. USA 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones, et al., Nature 321:522-525 (1986); Reichmann, et al., Nature 332:323-329 (1988); and Presta, Curr. Op. Struct. Biol. 2:593-596 (1992) and Hansen, WO2006105062.

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains that enables the sFv to form the desired structure for antigen binding. For a review of sFv, see Pluckthun in The Pharmacology of Monoclonal Antibodies, vol. 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger, et al., Proc. Natl. Acad. Sci. USA 90:6444-6448 (1993).

The expression "linear antibodies" when used throughout this application refers to the antibodies described in Zapata, et al. Protein Eng. 8(10):1057-1062 (1995). Briefly, these antibodies comprise a pair of tandem Fd segments ($V_H$-$C_H$1-$V_H$-$C_H$1) that form a pair of antigen binding regions. Linear antibodies can be bispecific or monospecific.

A "variant" anti-sphingolipid antibody, refers herein to a molecule which differs in amino acid sequence from a "parent" anti-sphingolipid antibody amino acid sequence by virtue of addition, deletion, and/or substitution of one or more amino acid residue(s) in the parent antibody sequence and retains at least one desired activity of the parent anti-binding antibody. Desired activities can include the ability to bind the antigen specifically, the ability to inhibit proleration in vitro, the ability to inhibit angiogenesis in vivo, and the ability to alter cytokine profile in vitro. In one embodiment, the variant comprises one or more amino acid substitution(s) in one or more hypervariable region(s) of the parent antibody. For example, the variant may comprise at least one, e.g. from about one to about ten, and preferably from about two to about five, substitutions in one or more hypervariable regions of the parent antibody. Ordinarily, the variant will have an amino acid sequence having at least 50% amino acid sequence identity with the parent antibody heavy or light chain variable domain sequences, more preferably at least 65%, more preferably at least 75%, more preferably at least 80%, more preferably at least 85%, more preferably at least 90%, and most preferably at least 95% sequence identity. Identity or homology with respect to this sequence is defined herein as the percentage of amino acid residues in the candidate sequence that are identical with the parent antibody residues, after aligning the sequences and introducing gaps, if necessary, to achieve the maximum percent sequence identity. None of N-terminal, C-terminal, or internal extensions, deletions, or insertions into the antibody sequence shall be construed as affecting sequence identity or homology. The variant retains the ability to bind a sphingolipid and preferably has desired activities which are superior to those of the parent antibody. For example, the variant may have a stronger binding affinity, enhanced ability to reduce angiogenesis and/or halt tumor progression. To analyze such desired properties (for example less immunogenic, longer half-life, enhanced stability, enhanced potency), one should compare a Fab form of the variant to a Fab form of the parent antibody or a full length form of the variant to a full length form of the parent antibody, for example, since it has been found that the format of the anti-sphingolipid antibody impacts its activity in the biological activity assays disclosed herein. The variant antibody of particular interest herein can be one which displays at least about 5%, preferably at least about 10%, 25%, 59%, or more of at least one desired activity. The preferred variant is one that has superior biophysical properties as measured in vitro or superior activities biological as measured in vitro or in vivo when compared to the parent antibody.

The "parent" antibody herein is one that is encoded by an amino acid sequence used for the preparation of the variant. Preferably, the parent antibody has a human framework region and, if present, has human antibody constant region(s). For example, the parent antibody may be a humanized or human antibody.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The word "label" when used herein refers to a detectable compound or composition that is conjugated directly or indirectly to the antibody. The label may itself be detectable by itself (e.g., radioisotope labels or fluorescent labels) or, in the case of an enzymatic label, may catalyze chemical alteration of a substrate compound or composition that is detectable.

"Neuropathic pain" is a chronic pain state caused by pathologic changes in the nervous system.

A "patentable" composition, process, machine, or article of manufacture according to the invention means that the subject matter satisfies all statutory requirements for patentability at the time the analysis is performed. For example, with regard to novelty, non-obviousness, or the like, if later investigation reveals that one or more claims encompass one or more embodiments that would negate novelty, non-obviousness, etc., the claim(s), being limited by definition to "patentable" embodiments, specifically exclude the unpatentable embodiment(s). Also, the claims appended hereto are to be interpreted both to provide the broadest reasonable scope, as well as to preserve their validity. Furthermore, the claims are to be interpreted in a way that (1) preserves their validity and (2) provides the broadest reasonable interpretation under the circumstances, if one or more of the statutory requirements for patentability are amended or if the standards change for assessing whether a particular statutory requirement for patentability is satisfied from the time this application is filed or issues as a patent to a time the validity of one or more of the appended claims is questioned.

The term "pharmaceutically acceptable salt" refers to salts which retain the biological effectiveness and properties of the agents and compounds of this invention and which are not biologically or otherwise undesirable. In many cases, the agents and compounds of this invention are capable of forming acid and/or base salts by virtue of the presence of charged groups, for example, charged amino and/or carboxyl groups or groups similar thereto. Pharmaceutically acceptable acid addition salts may be prepared from inorganic and organic acids, while pharmaceutically acceptable base addition salts can be prepared from inorganic and organic bases. For a review of pharmaceutically acceptable salts (see Berge, et al. (1977) J. Pharm. Sci., vol. 66, 1-19).

A "plurality" means more than one.

The terms "separated", "purified", "isolated", and the like mean that one or more components of a sample contained in a sample-holding vessel are or have been physically removed from, or diluted in the presence of, one or more other sample components present in the vessel. Sample components that may be removed or diluted during a separating or purifying step include, chemical reaction products, unreacted chemicals, proteins, carbohydrates, lipids, and unbound molecules.

The term "species" is used herein in various contexts, e.g., a particular species of drug. In each context, the term refers to a population of chemically indistinct molecules of the sort referred in the particular context.

"Specifically associate" and "specific association" and the like refer to a specific, non-random interaction between two molecules, which interaction depends on the presence of structural, hydrophobic/hydrophilic, and/or electrostatic features that allow appropriate chemical or molecular interactions between the molecules.

A "subject" or "patient" refers to an animal in need of treatment that can be effected by molecules of the invention. Animals that can be treated in accordance with the invention include vertebrates, with mammals such as bovine, canine, equine, feline, ovine, porcine, and primate (including humans and non-human primates) animals being particularly preferred examples.

A "therapeutically effective amount" (or "effective amount") refers to an amount of an active ingredient, e.g., an agent according to the invention, sufficient to effect treatment when administered to a subject or patient. Accordingly, what constitutes a therapeutically effective amount of a composition according to the invention may be readily determined by one of ordinary skill in the art. In the context of ocular therapy, a "therapeutically effective amount" is one that produces an objectively measured change in one or more parameters associated with treatment of the ocular disease or condition including an increase or decrease in the expression of one or more genes correlated with the ocular disease or condition, induction of apoptosis or other cell death pathways, clinical improvement in symptoms, a decrease in aberrant neovascularization or in inflammation, etc. Of course, the therapeutically effective amount will vary depending upon the particular subject and condition being treated, the weight and age of the subject, the severity of the disease condition, the particular compound chosen, the dosing regimen to be followed, timing of administration, the manner of administration and the like, all of which can readily be determined by one of ordinary skill in the art. It will be appreciated that in the context of combination therapy, what constitutes a therapeutically effective amount of a particular active ingredient may differ from what constitutes a therapeutically effective amount of the active ingredient when administered as a monotherapy (ie., a therapeutic regimen that employs only one chemical entity as the active ingredient).

The term "treatment" or "treating" of a disease or disorder includes preventing or protecting against the disease or disorder (that is, causing the clinical symptoms not to develop); inhibiting the disease or disorder (i.e., arresting or suppressing the development of clinical symptoms; and/or relieving the disease or disorder (i.e., causing the regression of clinical symptoms). As will be appreciated, it is not always possible to distinguish between "preventing" and "suppressing" a disease or disorder since the ultimate inductive event or events may be unknown or latent. Accordingly, the term "prophylaxis" will be understood to constitute a type of "treatment" that encompasses both "preventing" and "suppressing." The term "treatment" thus includes "prophylaxis".

The term "therapeutic regimen" means any treatment of a disease or disorder using chemotherapeutic drugs, radiation therapy, surgery, gene therapy, DNA vaccines and therapy, antisense-based therapies including siRNA therapy, anti-angiogenic therapy, immunotherapy, bone marrow transplants, aptamers and other biologics such as antibodies and antibody variants, receptor decoys and other protein-based therapeutics.

SUMMARY OF THE INVENTION

The present application describes patentable methods of treating or preventing pain, which methods comprise administering to a subject, including a human subject, having or believed to be at risk of having pain, an antibody (or an antibody fragment or derivative) that binds and neutralizes S1P. The antibody may be a polyclonal or monoclonal antibody, or an antibody fragment or derivative, that retains binding ability for S1P. Preferred are humanized monoclonal antibodies or fragments thereof that bind S1P.

The instant methods are particularly useful for treating or preventing pain such as neuropathic pain, allodynia and hyperalgesia. Treatment of pain associated with chemotherapeutic drug treatment is one embodiment of the invention.

These and other aspects and embodiments of the invention are discussed in greater detail in the sections that follow. The foregoing and other aspects of the invention will become more apparent from the following detailed description, accompanying drawings, and the claims. Although methods and materials similar or equivalent to those described herein can be used in the practice or testing of the present invention, suitable methods and materials are described below. In addition, the materials, methods, and examples below are illustrative only and not intended to be limiting.

BRIEF DESCRIPTION OF THE DRAWINGS

A brief summary of each of the figures is provided below.

FIG. 1 is a line graph showing that, when compared to the vehicle group (□), administration of paclitaxel (●) led to a time-dependent development of mechano-allodynia, which was significantly attenuated at 16 h by intravenous delivery of LT1002 (▲), but not by control antibody LT1017 (▼). Results are expressed as mean±SEM. Behavioral data for 3 animals was analyzed by two-tailed, two-way ANOVA with Bonferroni post hoc comparisons to the paclitaxel group where *P<0.01 and **P<0.001 for paclitaxel vs vehicle and †P<0.05 for paclitaxel +LT1002 vs paclitaxel.

FIG. 2 is a line graph showing that when compared to rats given intraplantar injection of saline (antibody vehicle, Veh, Δ, n=3), an intraplantar injection of ceramide (10 ug, ◇, n=3) led to a time-dependent development of thermal hyperalgesia that was attenuated by the anti-S1P antibody LT1002 (242 ug, ●, n=3) but not by isotype control antibody LT1017 (286 ug, ■, n=3). Given alone, LT1002 (○, n=3) or LT1017 (□, n=3) had no effect.

DETAILED DESCRIPTION OF THE INVENTION

Figure 1:
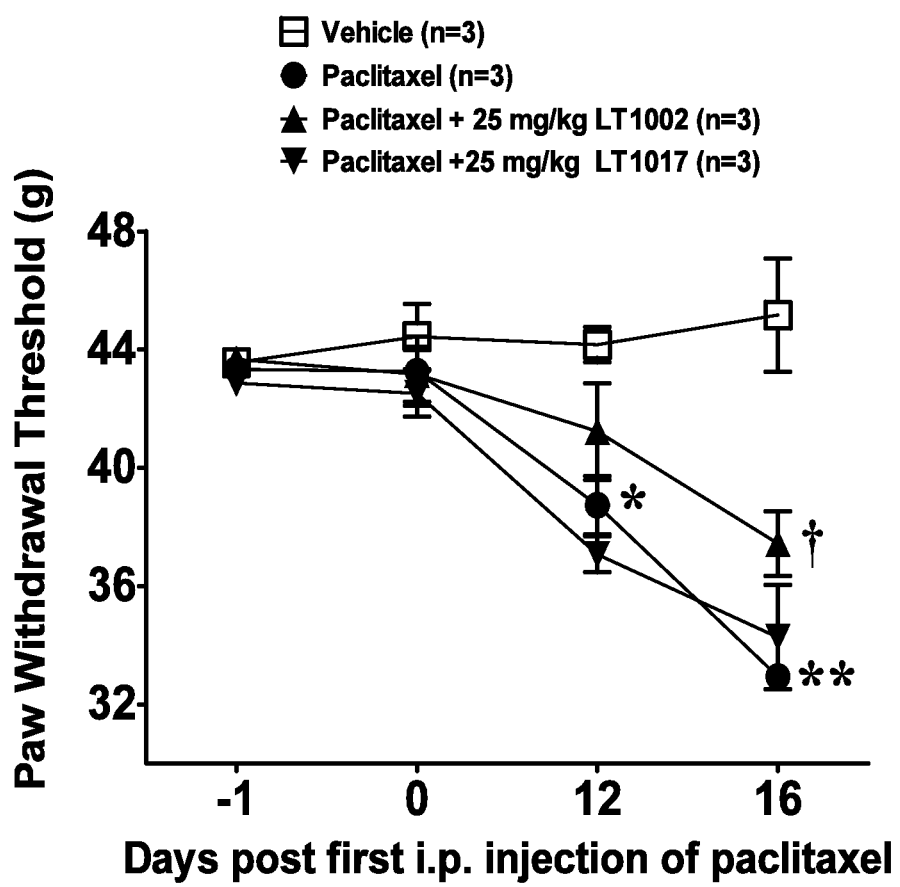
FIG. 1: Anti-S1P antibody LT1002 but not control antibody blocks paclitaxel-induced neuropathic pain.

Compounds.

The present invention describes certain anti-S1P agents, particularly those that are immune-derived moieties, including antibodies, which are specifically reactive with the bioactive lipid S1P; in other words, the bioactive lipid to which the anti-S1P agent reacts is S1P.

Antibody molecules or immunoglobulins are large glycoprotein molecules with a molecular weight of approximately 150 kDa, usually composed of two different kinds of polypeptide chain. One polypeptide chain, termed the "heavy" chain (H) is approximately 50 kDa. The other polypeptide, termed the "light" chain (L), is approximately 25 kDa. Each immunoglobulin molecule usually consists of two heavy chains and two light chains. The two heavy chains are linked to each other by disulfide bonds, the number of which varies between the heavy chains of different immunoglobulin isotypes. Each light chain is linked to a heavy chain by one covalent disulfide bond. In any given naturally occurring antibody molecule, the two heavy chains and the two light chains are identical, harboring two identical antigen-binding sites, and are thus said to be divalent, i.e., having the capacity to bind simultaneously to two identical molecules.

The "light" chains of antibody molecules from any vertebrate species can be assigned to one of two clearly distinct types, kappa (k) and lambda (l), based on the amino acid sequences of their constant domains. The ratio of the two types of light chain varies from species to species. As a way of example, the average k to l ratio is 20:1 in mice, whereas in humans it is 2:1 and in cattle it is 1:20.

The "heavy" chains of antibody molecules from any vertebrate species can be assigned to one of five clearly distinct types, called isotypes, based on the amino acid sequences of their constant domains. Some isotypes have several subtypes. The five major classes of immunoglobulin are immunoglobulin M (IgM), immunoglobulin D (IgD), immunoglobulin G (IgG), immunoglobulin A (IgA), and immunoglobulin E (IgE). IgG is the most abundant isotype and has several subclasses (IgG1, 2, 3, and 4 in humans). The Fc fragment and hinge regions differ in antibodies of different isotypes, thus determining their functional properties. However, the overall organization of the domains is similar in all isotypes.

The term "variable region" refers to the N-terminal portion of the antibody molecule or a fragment thereof. In general, each of the four chains has a variable (V) region in its amino terminal portion, which contributes to the antigen-binding site, and a constant (C) region, which determines the isotype. The light chains are bound to the heavy chains by many noncovalent interactions and by disulfide bonds and the V regions of the heavy and light chains pair in each arm of antibody molecule to generate two identical antigen-binding sites. Some amino acid residues are believed to form an interface between the light- and heavy-chain variable domains [see Kabat, et al. (1991), Sequences of Proteins of Immunological Interest, Fifth Edition, National Institute of Health, Bethesda, Md. and Clothia et al. (1985), J. Mol. Biol, vol 186: 651].

Of note, variability is not uniformly distributed throughout the variable domains of antibodies, but is concentrated in three segments called "complementarity-determining regions" (CDRs) or "hypervariable regions" both in the light-chain and the heavy-chain variable domains. The more highly conserved portions of variable domains are called the "framework region" (FR). The variable domains of native heavy and light chains each comprise four FR regions connected by three CDRs. The CDRs in each chain are held together in close proximity by the FR regions and, with the CDRs from the other chains, form the antigen-binding site of antibodies [see Kabat, et al. (1991), Sequences of Proteins of Immunological Interest, Fifth Edition, National Institute of Health, Bethesda, Md.]. Collectively, the 6 CDRs contribute to the binding properties of the antibody molecule for the antigen. However, even a single variable domain (or half of an Fv, comprising only three CDRs specific for an antigen) has the ability to recognize and bind antigen [see Pluckthun (1994), in The Pharmacology of Monoclonal Antibodies, vol. 113, Rosenburg and Moore eds., Springer-Verlag, New York, pp. 269-315].

The term "constant domain" refers to the C-terminal region of an antibody heavy or light chain. Generally, the constant domains are not directly involved in the binding properties of an antibody molecule to an antigen, but exhibit various effector functions, such as participation of the antibody in antibody-dependent cellular toxicity. Here, "effector functions" refer to the different physiological effects of antibodies (e.g., opsonization, cell lysis, mast cell, basophil and eosinophil degranulation, and other processes) mediated by the recruitment of immune cells by the molecular interaction between the Fc domain and proteins of the immune system. The isotype of the heavy chain determines the functional properties of the antibody. Their distinctive functional properties are conferred by the carboxy-terminal portions of the heavy chains, where they are not associated with light chains.

As used herein, "antibody fragment" refers to a portion of an intact antibody that includes the antigen binding site or variable regions of an intact antibody, wherein the portion can be free of the constant heavy chain domains (e.g., CH2, CH3, and CH4) of the Fc region of the intact antibody. Alternatively, portions of the constant heavy chain domains (e.g., CH2, CH3, and CH4) can be included in the "antibody fragment". Examples of antibody fragments are those that retain antigen-binding and include Fab, Fab', F(ab')2, Fd, and Fv fragments; diabodies; triabodies; single-chain antibody molecules (sc-Fv); minibodies, nanobodies, and multispecific antibodies formed from antibody fragments. By way of example, a Fab fragment also contains the constant domain of a light chain and the first constant domain (CH1) of a heavy chain.

The term "variant" refers to an amino acid sequence which differs from the native amino acid sequence of an antibody by at least one amino acid residue or modification. A native or parent or wild-type amino acid sequence refers to the amino acid sequence of an antibody found in nature. "Variant" of the antibody molecule includes, but is not limited to, changes within a variable region or a constant region of a light chain and/or a heavy chain, including the hypervariable or CDR region, the Fc region, the Fab region, the CH1 domain, the CH2 domain, the CH3 domain, and the hinge region.

The term "specific" refers to the selective binding of an antibody to its target epitope. Antibody molecules can be tested for specificity of binding by comparing binding of the antibody to the desired antigen to binding of the antibody to unrelated antigen or analogue antigen or antigen mixture under a given set of conditions. Preferably, an antibody according to the invention will lack significant binding to unrelated antigens, or even analogs of the target antigen. Here, the term "antigen" refers to a molecule that is recognized and bound by an antibody molecule or immune-derived moiety that binds to the antigen. The specific portion of an antigen that is bound by an antibody is termed the "epitope." A "hapten" refers to a small molecule that can, under most circumstances, elicit an immune response (i.e., act as an antigen) only when attached to a carrier molecule, for example, a protein, polyethylene glycol (PEG), colloidal gold, silicone beads, and the like. The carrier may be one that also does not elicit an immune response by itself.

The term "antibody" is used in the broadest sense, and encompasses monoclonal, polyclonal, multispecific (e.g., bispecific, wherein each arm of the antibody is reactive with a different epitope or the same or different antigen), minibody, heteroconjugate, diabody, triabody, chimeric, and synthetic antibodies, as well as antibody fragments that specifically bind an antigen with a desired binding property and/or biological activity.

The term "monoclonal antibody" (mAb) refers to an antibody, or population of like antibodies, obtained from a population of substantially homogeneous antibodies, and is not to be construed as requiring production of the antibody by any particular method. For example, monoclonal antibodies can be made by the hybridoma method first described by Kohler and Milstein (1975), Nature, vol 256: 495-497, or by recombinant DNA methods.

The term "chimeric" antibody (or immunoglobulin) refers to a molecule comprising a heavy and/or light chain which is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity [Cabilly et al. (1984), infra; Morrison et al., Proc. Natl. Acad. Sci. U.S.A. 81:6851].

The term "humanized antibody" refers to forms of antibodies that contain sequences from non-human (eg, murine) antibodies as well as human antibodies. A humanized antibody can include conservative amino acid substitutions or non-natural residues from the same or different species that do not significantly alter its binding and/or biologic activity. Such antibodies are chimeric antibodies that contain minimal sequence derived from non-human immunoglobulins. For the most part, humanized antibodies are human immunoglobulins (recipient antibody) in which residues from a complementary-determining region (CDR) of the recipient are replaced by residues from a CDR of a non-human species (donor antibody) such as mouse, rat, camel, bovine, goat, or rabbit having the desired properties. Furthermore, humanized antibodies can comprise residues that are found neither in the recipient antibody nor in the imported CDR or framework sequences. These modifications are made to further refine and maximize antibody performance. Thus, in general, a humanized antibody will comprise all of at least one, and in one aspect two, variable domains, in which all or all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), or that of a human immunoglobulin. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519,596 A1; Queen et al. (1989) Proc. Nat'l Acad. Sci. USA, vol 86:10029-10033).

The term "bispecific antibody" can refer to an antibody, or a monoclonal antibody, having binding properties for at least two different epitopes. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. Alternatively, bispecific antibodies can be prepared using chemical linkage. Bispecific antibodies include bispecific antibody fragments.

The term "heteroconjugate antibody" can refer to two covalently joined antibodies. Such antibodies can be prepared using known methods in synthetic protein chemistry, including using crosslinking agents. As used herein, the term "conjugate" refers to molecules formed by the covalent attachment of one or more antibody fragment(s) or binding moieties to one or more polymer molecule(s).

The term "biologically active" refers to an antibody or antibody fragment that is capable of binding the desired epitope and in some way exerting a biologic effect. Biological effects include, but are not limited to, the modulation of a growth signal, the modulation of an anti-apoptotic signal, the modulation of an apoptotic signal, the modulation of the effector function cascade, and modulation of other ligand interactions.

The term "recombinant DNA" refers to nucleic acids and gene products expressed therefrom that have been engineered, created, or modified by man. "Recombinant" polypeptides or proteins are polypeptides or proteins produced by recombinant DNA techniques, for example, from cells transformed by an exogenous DNA construct encoding the desired polypeptide or protein. "Synthetic" polypeptides or proteins are those prepared by chemical synthesis.

The term "expression cassette" refers to a nucleotide molecule capable of effecting expression of a structural gene (i.e., a protein coding sequence, such as an antibody of the invention) in a host compatible with such sequences. Expression cassettes include at least a promoter operably linked with the polypeptide-coding sequence, and, optionally, with other sequences, e.g., transcription termination signals. Additional regulatory elements necessary or helpful in effecting expression may also be used, e.g., enhancers. Thus, expression cassettes include plasmids, expression vectors, recombinant viruses, any form of recombinant "naked DNA" vector, and the like.

Sources of antibody are not limited to those exemplified herein (e.g., murine and humanized murine antibody). Antibodies may be raised in many species including mammalian species (for example, mouse, rat, camel, bovine, goat, horse, guinea pig, hamster, sheep and rabbit) and birds (duck, chicken). Antibodies raised may derive from a different species from the animal in which they are raised. For example, the XenoMouse™ (Abgenix, Inc., Fremont Calif.) produces fully human monoclonal antibodies. For certain purposes, native human antibodies, such as autoantibodies to S1P isolated from individuals who may show a titer of such S1P autoantibody may be used. Alternatively, a human antibody sequence library may be used to generate antibodies comprising a human sequence.

Antibody Generation and Characterization

Generation of anti-S1P antibodies, humanized anti-S1P antibodies and variants thereof are described, e.g., in U.S. Pat. No. 8,026,342 which is commonly owned with the instant application and is incorporated herein by reference in its entirety. Methods for determining antibody are also described therein. Preferred humanized or variant antibodies are those which bind S1P with a $K_d$ value of no more than about $1 \times 10^{-7}$ M, preferably no more than about $1 \times 10^{-8}$ M, and most preferably no more than about $5 \times 10^{-9}$ M. Sequences of several preferred anti-S1P antibodies are shown in U.S. Pat. No. 8,026,342.

Aside from antibodies with strong binding affinity for S1P, it is also desirable to select humanized or variant antibodies that have other beneficial properties from a therapeutic perspective. For example, the antibody may be one that reduces inflammation.

A preferred formulation for systemic administration of the anti-S1P antibodies is disclosed in provisional patent application U.S. 61/042,736, "Pharmaceutical Compositions for Binding Sphingosine-1-Phosphate", filed Apr. 5, 2008, and commonly owned with the instant invention, which is incorporated herein in its entirety.

Applications

The invention is drawn to compositions and methods for treating or preventing pain, using one or more therapeutic agents, e.g., antibodies, that bind S1P. These therapeutic methods and compositions act by changing the effective concentration, i.e., the absolute, relative, effective and/or available concentration and/or activities, of certain undesired bioactive lipids. Lowering the effective concentration of the bioactive lipid may be said to "neutralize" the target lipid or its undesired effects, including downstream effects. Here, "undesired" refers to a bioactive lipid that is unwanted due to its involvement in a disease process, for example, as a signaling molecule, or to an unwanted amount of a bioactive lipid which contributes to disease when present in excess.

Without wishing to be bound by any particular theory, it is believed that inappropriate concentrations of S1P and/or its metabolites or downstream effectors, may cause or contribute to the development of various diseases and disorders. As such, the compositions and methods can be used to treat these diseases and disorders, particularly by decreasing the effective in vivo concentration of S1P. In particular, it is believed that the compositions and methods of the invention are useful in treating and/or preventing pain, including neuropathic pain and inflammatory pain. It will be appreciated that many diseases and conditions are characterized, at least in part, by multiple pathological processes and that the classifications provided herein are for descriptive convenience and do not limit the invention.

Antibodies as Drugs

The use of monoclonal antibodies (mAbs) as a therapeutic treatment for a variety of diseases and disorders is rapidly increasing because they have been shown to be safe and efficacious therapeutic agents. Approved therapeutic mAbs include Avastin®, Erbitux®, and Rituxan®. Additional mAbs are in various phases of clinical development for a variety of diseases with the majority targeting various forms of cancer. In general, monoclonal antibodies are generated in non-human mammals. The therapeutic utility of murine monoclonal antibodies is limited, however, principally due to the fact that human patients mount their own antibody response to murine antibodies. This response, the so-called HAMA (human anti-mouse antibody) response, results in the eventual neutralization and rapid elimination of murine mAbs. This limitation has been overcome with the development of a process called "humanization" of murine antibodies. Humanization greatly lessens the development of an immune response against the administered therapeutic MAb and thereby avoids the reduction of half-life and therapeutic efficacy consequent on HAMA. For the most part, the humanization process consists of grafting the murine complementary determining regions (CDRs) into the framework region (FR) of a human immunoglobulin. This strategy is referred to as "CDR grafting". "Backmutation" to murine amino acid residues of selected residues in the human FR is often required to regain affinity that is lost in the initial grafted construct.

The manufacture of mAbs is a complex process that stems from the variability of the protein itself. The variability of mAbs can be localized to the protein backbone and/or to the carbohydrate moiety. The heterogeneity can be attributed to the formation of alternative disulfide pairings, deamidation and the formation of isoaspartyl residues, methionine and cysteine oxidation, cyclization of N-terminal glutamine residues to pyroglutamate and partial enzymatic cleavage of C-terminal lysines by mammalian carboxypeptidases. Engineering is commonly applied to antibody molecules to improve their properties, such as enhanced stability, resistance to proteases, aggregation behavior and enhance the expression level in heterologous systems.

The murine anti-S1P mAb was humanized by grafting the six CDRs from Lpath's murine anti-S1P antibody, LT1002 (sphingomab), into a human framework. Further modifications were engineered to further refine and optimize the antibody performance. The humanized mAb, LT1009 (sonepcizumab) presented the same characteristics as the LT1002 and is thus suitable for testing in clinical trials.

One way to control the amount of undesirable sphingolipids, e.g., undesired levels of S1P, in a patient is by providing a composition that comprises one or more humanized antisphingolipid antibodies to bind one or more sphingolipids, thereby acting as therapeutic "sponges" that reduce the level of free undesirable sphingolipids. When a compound is referred to as "free", the compound is not in any way restricted from reaching the site or sites where it exerts its undesirable effects. Typically, a free compound is present in blood and tissue, which either is or contains the site(s) of action of the free compound, or from which a compound can freely migrate to its site(s) of action. A free compound may also be available to be acted upon by any enzyme that converts the compound into an undesirable compound.

S1P and Pain

S1P has been associated with a number of diseases and conditions, such as cancer, cardiovascular disease, aberrant angiogenesis, inflammation and pain. The roles of S1P in disease are summarized, for example, in U.S. Pat. No. 8,026,342 which is commonly owned with the instant invention and incorporated by reference herein in its entirety.

Pain is the most common reason for doctor visits in the US and is present as part of a broad spectrum of diseases, disorders and conditions. Pain may be acute or chronic and may be classified according to location in the body and/or by etiology, although in many cases the etiology of pain is not understood or may be due to several possible causes, which may overlap. Pain may also be described qualitatively, as allodynia (abnormal sensory perception of pain) or hyperalgesia (exaggerated pain sensations), for example.

Neuropathic pain is a complex, often chronic form of pain associated with damage or dysfunction of the nervous system. Simply stated, neuropathic pain is a chronic pain state caused by pathological changes in the nervous system. Myers, et al (2006) Drug Disc. Today 11: 8-20. Causes of acute and/or chronic neuropathic pain include, but are not limited to, injury, trauma, or damage to the central or peripheral nervous system (e.g., spinal cord injury, disc herniation, multiple sclerosis or other degenerative or neurodegenerative disease), inflammation, drug exposure (for example, cytotoxics such as paclitaxel (TAXOL), cisplatin, and other chemotherapeutic agents), diabetes, viral disease (such as, for example, HIV and herpes zoster), metabolic disease, severe ischemic insults, nutrient deficiency, toxin exposure, and cancer. Cancer neuropathic pain may result directly from tumor impingement on nerves, or indirectly such as from radiation, surgery, or drug treatment. Neuropathic pain is mediated through neuroinflammatory mechanisms controlled by inflammatory responses to the initial insult and affecting nervous system tissue. Myers, et al (2006), Drug Disc. Today 11: 8-20. Many inflammatory mediators, such as TNFα, have been found to be pivotal in neuropathic pain. Leung L, Cahill C M. (2010) J. Neuroinflamm., 7:27. Neuropathic pain is unresponsive to most common painkillers.

Pain associated with chemotherapy is a major dose-limiting toxicity of many small molecule chemotherapeutic agents, particularly the cytotoxics. For instance, paclitaxel (TAXOL), an anti-neoplastic agent derived from the Pacific yew tree *Taxus brevifolia*, is used to treat a variety of cancers, including ovarian, breast, and non-small cell lung cancer. paclitaxel's effectiveness, however, is limited by the highly incidental development of severe painful peripheral neuropathy such as numbness and burning pain. An antibody against a bioactive lipid correlated with such pain, for example, S1P (or a derivative of such an antibody that contains a lipid-binding portion thereof), could be administered in combination with paclitaxel in order to reduce the pain associated with the chemotherapeutic agent. As a result of ameliorating this dose-limiting toxicity, the amount of paclitaxel to be administered could be even higher (and thus even more effective) when used in combination with such a monoclonal antibody or antibody derivative. In some embodiments, the chemotherapeutic agent (or other drug) could be conjugated to or otherwise associated with the antibody or antibody derivative, for example, by covalently linking the small molecule chemotherapeutic agent to the antibody, by linking the small molecule chemotherapeutic to a multivalent scaffold to which is also linked a monoclonal antibody or at least one bioactive lipid binding domain derived from a monoclonal antibody specifically reactive against the target bioactive lipid, etc.

Diabetic neuropathy in type 1 and 2 diabetes in both humans and animal models is characterized by pathophysiological changes in all components (sensory, motor and autonomic) of the peripheral nervous system. In addition to the changes of primary afferent nerves, central sensitization is believed to be an important mechanism underlying persistent pain, including neuropathic and inflammatory pain. G. Baranauskas, A. Nistri (1998) Prog Neurobiol 54, 349; T. J. Coderre, R. Melzack (1992) J Neurosci 12, 3665; R. Dubner, M. A. Ruda (1992) Trends Neurosci 15, 96; M. J. Millan (1999) Prog Neurobiol 57, 1; C. J. Woolf, S. W. Thompson, (1991) Pain 44, 293.

One of the key features of inflammatory states is that normally innocuous stimuli produce pain. This pain is often referred to as "inflammatory pain." Pain arising from inflamed or injured tissues may arise spontaneously in the absence of an external trigger. Alternatively, responses to noxious stimuli may be enhanced (hyperalgesia) or normally innocuous stimuli may produce pain (allodynia).

Inflammatory mediators are involved in the genesis, persistence, and severity of pain. IL-6 is a potent pain-generating inflammatory mediator. IL-6 is produced in the rat spinal cord following peripheral nerve injury, with levels of IL-6 levels correlating directly with the intensity of allodynia. Arruda, et al. (2000), Brain Res. 879:216-25. IL-6 levels increase during stress or inflammation, and rheumatoid arthritis is associated with increased levels of IL-6 in synovial fluid. Matsumoto, et al (2006), Rheumatol. Int. 26:1096-1100; Desgeorges, et al. (1997), J. Rheumatol. 24:1510-1516. Neuropathic pain is prevented in IL-6 knockout mice. Xu, et al (1997), Cytokine 9:1028-1033.

IL-8 is a pain-generating inflammatory mediator. Drug treatment of post-herpetic neuralgia showed a decrease of 50% in IL-8 concentrations, and this decrease correlated with pain relief. Kotani, et al. (2000), New Engl. J. Med. 343:1514-1519.

TNF-α induces axonal damage, macrophage recruitment and ectopic activity in peripheral nerve fibers and plays a role in the generation of hyperalgesia. TNFα is upregulated at the site of peripheral nerve lesions and in patients with neuropathic pain. Thalidomide, a selective blocker of TNF production, reduces hyperalgesia in an animal model of neuropathic pain (chronic constriction injury). George, et al. (2000), Pain 88:267-275.

A significant role of S1P in the development of pain was established using various pharmacological and genetic approaches. S1P is part of the ceramide metabolic pathway; ceramide is a potent proinflammatory sphingolipid which can be metabolized by ceramidase to sphingosine which can be converted to S1P by sphingosine kinase. As reviewed in Doyle et al. (2011) [Neurosci Lett. 499:4-8], ceramide has a well established role in inflammation, and experimental data also point to a role for ceramide in peripheral sensitization and both mechanical and thermal hyperalgesia. Doyle et al (2011) FASEB J. 25: 2782-2791; Joseph and Levine (2004) Eur. J. Neurosci. 20:2896-2902. Furthermore, TNF-alpha-mediated peripheral sensitization and nerve growth factor-induced sensitization of sensory neurons also involves ceramide. Zhang et al (2002) J. Physiol. 544:385-402. S1P also contributes to excitation of sensory neurons both in vitro and in vivo. Zhang et al. (2006) J. Physiol 575:101-113; Zhang et al (2006) J. Neurophysiol. 96:1042-1052; Zhang et al. (2002) J. Physiol. 544:385-402. Doyle et al. (2011) [Pain 152:643-648] have shown that intraplantar injection of S1P in rats led to the development of hyperalgesia. This effect is abrogated by genetic deletion of $S1PR_1$ (S1P receptor1) in neurons. Mair et al (2011) PLoS One 6:e17268.

Diabetic neuropathy in type 1 and 2 diabetes in both humans and animal models is characterized by pathophysiological changes in all components (sensory, motor and autonomic) of the peripheral nervous system. In addition to the changes of primary afferent nerves, central sensitization is believed to be an important mechanism underlying persistent pain, including neuropathic and inflammatory pain. G. Baranauskas, A. Nistri (1998) Prog Neurobiol 54, 349; T. J. Coderre, R. Melzack (1992) J Neurosci 12, 3665; R. Dubner, M. A. Ruda (1992) Trends Neurosci 15, 96; M. J. Millan (1999) Prog Neurobiol 57, 1; C. J. Woolf, S. W. Thompson, (1991) Pain 44, 293.

Formulations

Anti-sphingolipid antibodies may be formulated in a pharmaceutical composition that are useful for a variety of purposes, including the treatment of diseases, disorders or physical trauma. Pharmaceutical compositions comprising one or more humanized anti-sphingolipid antibodies of the invention may be incorporated into kits and medical devices for such treatment. Medical devices may be used to administer the pharmaceutical compositions of the invention to a patient in need thereof, and according to one embodiment of the invention, kits are provided that include such devices. Such devices and kits may be designed for routine administration, including self-administration, of the pharmaceutical compositions of the invention. Such devices and kits may also be designed for emergency use, for example, in ambulances or emergency rooms, or during surgery, or in activities where injury is possible but where full medical attention may not be immediately forthcoming (for example, hiking and camping, or combat situations).

Methods and Routes of Administration

The treatment for diseases and conditions discussed herein can be achieved by administering agents and compositions of the invention by various routes employing different formulations and devices. Suitable pharmaceutically acceptable diluents, carriers, and excipients are well known in the art.

One skilled in the art will appreciate that the amounts to be administered for any particular treatment protocol can readily be determined. Suitable amounts might be expected to fall within the range of 10 µg/dose to 10 g/dose, preferably within 10 mg/dose to 1 g/dose.

Drug substances may be administered by techniques known in the art, including but not limited to systemic, subcutaneous, intradermal, mucosal, including by inhalation, and topical administration. The mucosa refers to the epithelial tissue that lines the internal cavities of the body. For example, the mucosa comprises the alimentary canal, including the mouth, esophagus, stomach, intestines, and anus; the respiratory tract, including the nasal passages, trachea, bronchi, and lungs; and the genitalia. For the purpose of this specification, the mucosa also includes the external surface of the eye, i.e., the cornea and conjunctiva. Local administration (as opposed to systemic administration) may be advantageous because this approach can limit potential systemic side effects, but still allow therapeutic effect.

Pharmaceutical compositions used in the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations used in the present invention may be prepared according to conventional techniques well known in the pharmaceutical industry. Such techniques include the step of bringing into association the active ingredients with the pharmaceutical carrier(s) or excipient(s). Preferred carriers include those that are pharmaceutically acceptable, particularly when the composition is intended for therapeutic use in humans. For non-human therapeutic applications (e.g., in the treatment of companion animals, livestock, fish, or poultry), veterinarily acceptable carriers may be employed. In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment the pharmaceutical compositions may be formulated and used as foams. Pharmaceutical foams include formulations such as, but not limited to, emulsions, microemulsions, creams, jellies, and liposomes.

While basically similar in nature these formulations vary in the components and the consistency of the final product. The know-how on the preparation of such compositions and formulations is generally known to those skilled in the pharmaceutical and formulation arts and may be applied to the formulation of the compositions of the present invention.

Therapeutic Uses

For therapeutic applications, the anti-sphingolipid antibodies of the invention are administered to a mammal, preferably a human, in a pharmaceutically acceptable dosage form such as those discussed above, including those that may be administered to a human intravenously as a bolus or by continuous infusion over a period of time, by intramuscular, intraperitoneal, intra-cerebrospinal, subcutaneous, intra-articular, intrasynovial, intrathecal, oral, topical, or inhalation routes.

For the prevention or treatment of disease, the appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 ug/kg to about 50 mg/kg (e.g., 0.1-20 mg/kg) of antibody is an initial candidate dosage for administration to the patient, whether, for example, by one or more separate administrations, or by continuous infusion. A typical daily or weekly dosage might range from about 1 µg/kg to about 20 mg/kg or more, depending on the factors mentioned above. For repeated administrations over several days or longer, depending on the condition, the treatment is repeated until a desired suppression of disease symptoms occurs. However, other dosage regimens may be useful. The progress of this therapy is easily monitored by conventional techniques and assays, including, for example, radiographic imaging.

According to another embodiment of the invention, the effectiveness of the antibody in preventing or treating disease may be improved by administering the antibody serially or in combination with another agent that is effective for those purposes, such as conventional analgesics and drugs such as tricyclic antidepressants and anticonvulsants (e.g., gabapentin), which are sometimes administered for relief of neuropathic pain, for example. Such other agents may be present in the composition being administered or may be administered separately. The antibody is suitably administered serially or in combination with the other agent.

Articles of Manufacture

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the anti-sphingolipid antibody. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The invention will be better understood by reference to the following Examples, which are intended to merely illustrate the best mode now known for practicing the invention. The scope of the invention is not to be considered limited thereto.

EXAMPLES

Example 1

Antibody to S1P Reduces Paclitaxel-Induced Neuropathic Pain

Paclitaxel-induced neuropathic pain and drug administration: The well characterized rat model developed by Bennett was used, in which repeated intraperitoneal (i.p) injections of low doses of paclitaxel induce neuropathic pain (mechano-allodynia) with little systemic toxicity or motor impairment. Flatters, S. J. & Bennett, G. J. (2006) Pain 122, 245-257; Jin, H. W. et al. (2008) Exp Neurol 210, 229-237; Polomano, R. C., et al. (2001) Pain 94, 293-304.

The behavioral responses last for several weeks to months, thus modeling painful neuropathies in patients (ibid). Male Sprague Dawley rats (200-210 g starting weight) from Harlan (Indianapolis, Ind.) were housed 3-4 per cage in a controlled environment (12 h light/dark cycle) with food and water available ad libitum. All experiments were performed in accordance with the International Association for the Study of Pain and the National Institutes of Health guidelines on laboratory animal welfare and the recommendations by Saint Louis University Institutional Animal Care and Use Committee. All experiments were conducted with the experimenters blinded to treatment conditions.

Paclitaxel or its vehicle (Cremophor EL and 95% dehydrated ethanol in 1:1 ratio) was injected i.p in rats on four alternate days that is day (D) 0, 2, 4 and 6 at 1 mg/kg on with a final cumulative dose of 4 mg/kg. 1-3 The following experimental test substances were used: LT1002, and its isotype control, LT1017; these were dissolved in saline and provided by Lpath in individual vials. Experimental test substances were given intravenously (i.v) at 25 mg/kg according to a dosing regimen designed by Lpath as follows (and see experimental design, schematic in power point format). Experimental test substances were given one day before (D-1) the first injection of paclitaxel, and subsequently on D2, D5, D8, D11 and D14 after the first injection of paclitaxel. Vehicle that was used to dissolve test substance (saline) was injected according to the same dosing paradigm in paclitaxel-treated group or its respective vehicle. If injections of experimental test substances coincided with the injection of paclitaxel (i.e. D2), experimental test substances were delivered 15 min before paclitaxel. Mechanical withdrawal thresholds were assessed with an electronic version of the von Frey test (dynamic plantar aesthesiometer, model 37450; Ugo Basile, Milan, Italy) on D-1 before experimental test substance injection, the day after (D0) and before the first i.p. injection of paclitaxel and subsequently on D12 and D16. To this end, each rat was placed in a Plexiglas chamber (28×40×35-cm, wire mesh floor) and allowed to acclimate for fifteen minutes. After acclimation, a servo-controlled mechanical stimulus (a pointed metallic filament) was applied to the plantar surface, which exerts a progressively increasing punctate pressure, reaching up to 50 g within 10 s. The pressure evoking a clear voluntary hind-paw withdrawal response was recorded automatically and taken as the mechanical threshold index. Mechanical threshold is assessed three times at each time point to yield a mean value, which is reported as mean absolute threshold (grams, g). The development of mechano-allodynia is evidenced by a significant ($P<0.05$) reduction in mechanical mean absolute paw-withdrawal thresholds (grams, g) at forces that failed to elicit withdrawal responses before paclitaxel treatment (baseline). Paclitaxel treatments results in bilateral allodynia (ibid). Because thresholds did not differ between left and right hind paws at any time point in any group, values from both paws were averaged for further analysis and data presentation. A total of six groups were used with n=3 rats/group.

Group 1: Vehicle instead of paclitaxel+saline
Group 2: Paclitaxel+saline
Group 3: Paclitaxel+LT1002
Group 4: Paclitaxel+LT1017

Paw withdrawal threshold (g) for groups 1-4 on (D-1) and before i.v injection of experimental test substances or their vehicle (saline) were (mean+/s.em): 43.6±0.296, 43.3±0.376, 43.7±0.333, and 42.9±0.219, respectively.

Statistical Analysis. Data are expressed as mean±SEM for 3 animals per group and analyzed by two-tailed, two-way ANOVA with Bonferroni post hoc comparisons to the paclitaxel group. *$P<0.05$, **$P<0.001$ paclitaxel vs. vehicle group.

Results

Effects of LT1002 and LT1017 on Paclitaxel-Induced Neuropathic Vain.

When compared to the vehicle treated group, administration of paclitaxel led to the development of mechano-allodynia (FIG. 1). The development of mechano-allodynia at 16 h was significantly attenuated by LT1002, but not by LT1017 (FIG. 1). Paclitaxel-induced neuropathic pain and drug administration: The well characterized rat model developed by Bennett in which repeated intraperitoneal (i.p) injections of low doses of paclitaxel induce neuropathic pain (mechano-allodynia) with little systemic toxicity or motor impairment. The behavioral responses last for several weeks to months, thus modeling painful neuropathies in patients. Paclitaxel or its vehicle (Cremophor EL and 95% dehydrated ethanol in 1:1 ratio) was injected i.p in rats on four alternate days that is day (D) 0, 2, 4 and 6 at 1 mg/kg on with a final cumulative dose of 4 mg/kg.1-3 The following experimental test substances were used: LT1002 and LT1017; these were dissolved in saline and provided by Lpath in individual vials. Experimental test substances were given intravenously (i.v) at 25 mg/kg according to a dosing regimen designed by Lpath as follows (and see experimental design, schematic in power point format). Experimental test substances were given one day before (D-1) the first injection of paclitaxel, and subsequently on D2, D5, D8, D11 and D14 after the first injection of paclitaxel. Vehicle that was used to dissolve test substance (saline) was injected according to the same dosing paradigm in paclitaxel-treated group or its respective vehicle. If injections of experimental test substances coincided with the injection of paclitaxel (i.e. D2), experimental test substances were delivered 15 min before paclitaxel. Mechanical withdrawal thresholds were assessed with an electronic version of the von Frey test (dynamic plantar aesthesiometer, model 37450; Ugo Basile, Milan, Italy) on D-1 before experimental test substance injection, the day after (D0) and before the first i.p. injection of paclitaxel and subsequently on D12 and D16. To this end, each rat was placed in a Plexiglas chamber (28×40×35-cm, wire mesh floor) and allowed to acclimate for fifteen minutes. After acclimation, a servo-controlled mechanical stimulus (a pointed metallic filament) was applied to the plantar surface, which exerts a progressively increasing punctate pressure, reaching up to 50 g within 10 s. The pressure evoking a clear voluntary hind-paw withdrawal response was recorded automatically and taken as the mechanical threshold index. Mechanical threshold is assessed three times at each time point to yield a mean value, which is reported as mean absolute threshold (grams, g). The development of mechano-allodynia is evidenced by a significant ($P<0.05$) reduction in mechanical mean absolute paw-withdrawal thresholds (grams, g) at forces that failed to elicit withdrawal responses before paclitaxel treatment (baseline). Paclitaxel treatments results in bilateral allodynia (ibid). Because thresholds did not differ between left and right hind paws at any time point in any group, values from both paws were averaged for further analysis and data presentation. A total of six groups were used with n=3 rats/group.

Group 1: Vehicle instead of paclitaxel+saline
Group 2: Paclitaxel+saline
Group 3: Paclitaxel+LT1002
Group 4: Paclitaxel+LT1017

Paw withdrawal threshold (g) for groups 1-6 on (D-1) and before i.v injection of experimental test substances or their vehicle (saline) were (mean+/s.em): 43.6±0.296, 43.3±0.376, 43.7±0.333 and 42.9±0.219, respectively.

Statistical Analysis. Data are expressed as mean±SEM for 3 animals per group and analyzed by two-tailed, two-way ANOVA with Bonferroni post hoc comparisons to the paclitaxel group. *$P<0.05$, **$P<0.001$ paclitaxel vs. vehicle group.

Results

Effects of LT1002 and LT1017 on paclitaxel-induced neuropathic pain. When compared to the vehicle treated group, administration of paclitaxel led to the development of mechano-allodynia (FIG. 1). The development of mechano-allodynia at 16 h was significantly attenuated by LT1002, but not by LT1017 (FIG. 1).

Paclitaxel-induced neuropathic pain and drug administration: The well characterized rat model developed by Bennett was used, in which repeated intraperitoneal (i.p) injections of low doses of paclitaxel induce neuropathic pain (mechano-allodynia) with little systemic toxicity or motor impairment. The behavioral responses last for several weeks to months, thus modeling painful neuropathies in patients. Paclitaxel or its vehicle (Cremophor EL and 95% dehydrated ethanol in 1:1 ratio) was injected i.p in rats on four alternate days that is day (D) 0, 2, 4 and 6 at 1 mg/kg on with a final cumulative dose of 4 mg/kg. The following experimental test substances were used: LT1002, LT1017, 504B3 and LT1015; these were dissolved in saline and provided by Lpath in individual vials. Experimental test substances were given intravenously (i.v) at 25 mg/kg according to a dosing regimen designed by Lpath as follows (and see experimental design, schematic in power point format). Experimental test substances were given one day before (D-1) the first injection of paclitaxel, and subsequently on D2, D5, D8, D11 and D14 after the first injection of paclitaxel. Vehicle that was used to dissolve test substance (saline) was injected according to the same dosing paradigm in paclitaxel-treated group or its respective vehicle. If injections of experimental test substances coincided with the injection of paclitaxel (i.e. D2), experimental test substances were delivered 15 min before paclitaxel. Mechanical withdrawal thresholds were assessed with an electronic version of the von Frey test (dynamic plantar aesthesiometer, model 37450; Ugo Basile, Milan, Italy) on D-1 before experimental test substance injection, the day after (D0) and before the first i.p. injection of paclitaxel and subsequently on D12 and D16. To this end, each rat was placed in a Plexiglas chamber (28×40×35-cm, wire mesh floor) and allowed to acclimate for fifteen minutes. After acclimation, a servo-controlled mechanical stimulus (a pointed metallic filament) was applied to the plantar surface, which exerts a progressively increasing punctate pressure, reaching up to 50 g within 10 s. The pressure evoking a clear voluntary hind-paw withdrawal response was recorded automatically and taken as the mechanical threshold index. Mechanical threshold is assessed three times at each time point to yield a mean value, which is reported as mean absolute threshold (grams, g). The development of mechano-allodynia is evidenced by a significant ($P<0.05$) reduction in mechanical mean absolute paw-withdrawal thresholds (grams, g) at forces that failed to elicit withdrawal responses before paclitaxel treatment (baseline). Paclitaxel treatments results in bilateral allodynia.[1-3] Because thresholds did not differ between left and right hind paws at any time point in any group, values from both paws were averaged for further analysis and data presentation. A total of four groups were used with n=3 rats/group.

Group 1: Vehicle instead of paclitaxel+saline
Group 2: Paclitaxel+saline
Group 3: Paclitaxel+LT1002
Group 4: Paclitaxel+LT1017
Group 5: Paclitaxel+504B3
Group 6: Paclitaxel+LT1015

Paw withdrawal threshold (g) for groups 1-6 on (D-1) and before i.v injection of experimental test substances or their vehicle (saline) were (mean+/s.em): 43.6±0.296, 43.3±0.376, 43.7±0.333 and 42.9±0.219, respectively.

Statistical Analysis. Data are expressed as mean±SEM for 3 animals per group and analyzed by two-tailed, two-way ANOVA with Bonferroni post hoc comparisons to the paclitaxel group. *$P<0.05$, **$P<0.001$ paclitaxel vs. vehicle group.

Results: effects of LT1002 and LT1017 on paclitaxel-induced neuropathic pain. When compared to the vehicle treated group, administration of paclitaxel led to the development of mechano-allodynia (FIG. 1). The development of mechano-allodynia at 16 h was significantly attenuated by LT1002, but not by the isotype control, LT1017 (FIG. 1). Thus an antibody to S1P was able to attenuate the development of neuropathic pain resulting from chemotherapeutic treatment.

Example 2

Antibody to S1P Reduces Thermal Hyperalgesia

As reviewed supra, intraplantar injection of ceramide in rats leads to peripheral sensitization and mechanical hyperalgesia (Joseph and Levine, 2004); S1P contributes to excitation of rat sensory neurons and ceramide levels can be at least partly regulated by conversion of ceramide to sphingosine and from there to S1P. For these reasons the role of S1P in ceramide induced thermal hyperalgesia was studied, using the anti-S1P antibody, LT1002. Doyle et al. (2011) J. Neurosci. 499:4-8.

Male Sprague Dawley rats (200-220 g) were purchased from Harlan (Indianapolis, Ind.), housed 3-4 per cage, and maintained in a controlled environment (12 h light/dark cycles) with food and water ad libitum. The murine anti-S1P monoclonal antibody (LT1002) or its isotype-matched control monoclonal antibody (LT1017) or their vehicle (saline) were given by intraplantar injection into the right hindpaw of rats 15 minutes before intraplantar injections of $C_2$ ceramide (D-erythro-Sphingosine, N-Acetyl, Calbiochem, La Jolla Calif.) or its vehicle, DMSO. Drugs were injected in a 5 ul injection volume using a Hamilton gouge needle (3.5") in lightly anesthetized rats (80% $CO_2$/20% $O_2$). Hyperalgesic responses to heat were determined by the Hargreaves' Method using a Basile Plantar Test (Ugo Basile, Comeria, Italy) with a cut-of latency of 20 s to prevent tissue damage. Hargreaves et al. (1988) Pain 32:77-88. Rats were individually confide to Plexiglas chambers and allowed to acclimate for 15 minutes prior to behavioral testing. A mobile infrared generator was positioned to deliver a thermal stimulus directly to an individual hindpaw from beneath the chamber. The withdrawal latency period of injected paws was determined with an electronic clock circuit and thermocouple. Two readings were taken for each paw to calculate a mean latency for each animal. Thermal hyperalgesia results are the mean latency for each group and are expressed as Paw Withdrawal Latency (PWL). All treatments were conducted with the experimenters blinded to treatment conditions.

Figure 2:
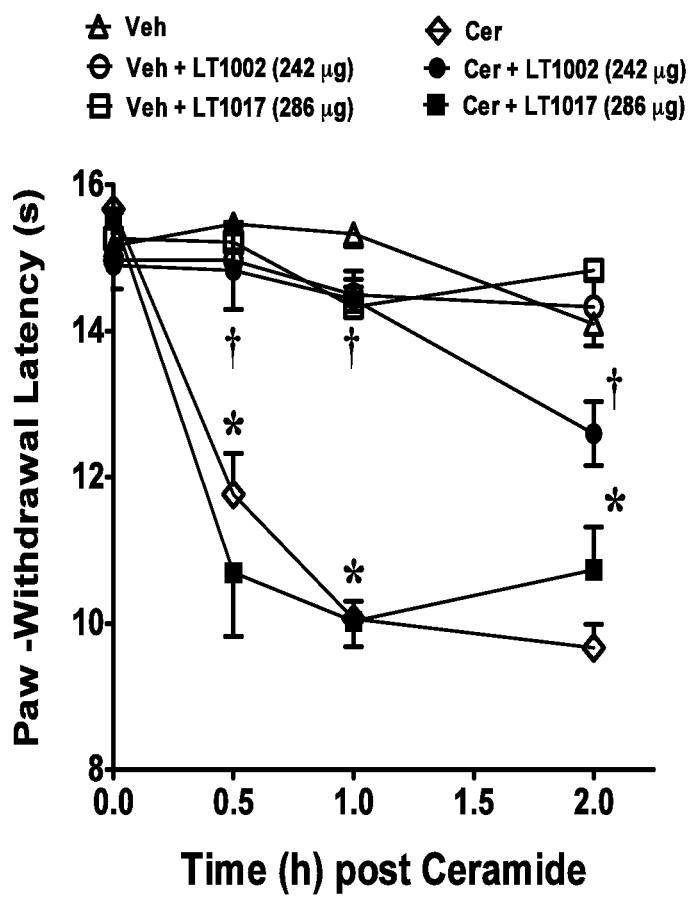
FIG. 2. Anti-S1P antibody LT1002 but not control antibody blocks ceramide-induced hyperalgesia.

Intraplantar injection of ceramide (10 ug, n=4), given at a dose previously shown to elicit mechanical and thermal hyperalgesia [Doyle et al (2011) FASEB J 25: 2782-2791, Joseph et al (2004) J. Neurosci. 20:2896-2902] led to a time-dependent development of thermal hyperalgesia that peaked by 2 hr. As shown in FIG. 2, This effect was blocked by anti-S1P antibody LT1002 (242 ug, n=3) but not by the isotype-matched control monoclonal antibody LT1017. When tested alone, neither the anti-S1P antibody (242 ug) nor the control antibody (286 ug) had any effect on baseline withdrawal latencies. S1P contributes to the hyperalgesic responses to ceramide, and thus S1P inhibitors such as antibody inhibitors of S1P are believed to be therapeutically useful in pain relief, including relief of inflammatory pain.

All of the compositions and methods described and claimed herein can be made and executed without undue experimentation in light of the present disclosure. While the compositions and methods of this invention have been described in terms of preferred embodiments, it will be apparent to those of skill in the art that variations may be applied to the compositions and methods. All such similar substitutes and modifications apparent to those skilled in the art are deemed to be within the spirit and scope of the invention as defined by the appended claims.

All patents, patent applications, and publications mentioned in the specification are indicative of the levels of those of ordinary skill in the art to which the invention pertains. All patents, patent applications, and publications, including those to which priority or another benefit is claimed, are herein incorporated by reference to the same extent as if each individual publication was specifically and individually indicated to be incorporated by reference.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of reducing, or reducing the development of, neuropathic pain, allodynia or hyperalgesia in a human subject, comprising administering to a human subject having or believed to be at risk of having pain an antibody or fragment thereof that binds and neutralizes sphingosine-1-phosphate (S1P), thereby reducing, or reducing the development of, neuropathic pain.

2. The method of claim 1 wherein the neuropathic pain is chemotherapeutic drug-induced neuropathic pain.

3. The method of claim 1 wherein the antibody is a monoclonal antibody.

4. The method of claim 3 wherein the antibody is a humanized antibody.

* * * * *